(12) United States Patent
Choi et al.

(10) Patent No.: US 12,161,892 B2
(45) Date of Patent: Dec. 10, 2024

(54) MASK APPARATUS AND METHOD FOR CONTROLLING THE SAME

(71) Applicant: LG Electronics Inc., Seoul (KR)

(72) Inventors: Hyengcheul Choi, Seoul (KR); Jinmoo Park, Seoul (KR); Seonghun Lee, Seoul (KR); Junchan Kwon, Seoul (KR); Taewook Kwon, Seoul (KR); Minsoo Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 807 days.

(21) Appl. No.: 17/245,534

(22) Filed: Apr. 30, 2021

(65) Prior Publication Data
US 2022/0016449 A1    Jan. 20, 2022

(30) Foreign Application Priority Data

Jul. 17, 2020    (KR) .................. 10-2020-0089132

(51) Int. Cl.
*A62B 18/00*    (2006.01)
*A62B 7/10*    (2006.01)
(Continued)

(52) U.S. Cl.
CPC .......... *A62B 18/006* (2013.01); *A62B 18/025* (2013.01); *A62B 18/08* (2013.01); *A62B 7/10* (2013.01); *A62B 23/02* (2013.01)

(58) Field of Classification Search
CPC ..... A62B 18/006; A62B 18/02; A62B 18/025; A62B 18/04; A62B 18/045; A62B 5/0816;
(Continued)

(56) References Cited

U.S. PATENT DOCUMENTS

| 4,546,793 A | 10/1985 | Stupecky |
| 4,646,732 A | 3/1987 | Chien |

(Continued)

FOREIGN PATENT DOCUMENTS

| CN | 1455270 | 11/2003 |
| CN | 103505788 | 1/2014 |

(Continued)

OTHER PUBLICATIONS

Extended European Search Report in European Appln. No. 21169773. 5, dated Sep. 24, 2021, 4 pages.

(Continued)

*Primary Examiner* — Valerie L Woodward
*Assistant Examiner* — Jaeick Jang
(74) *Attorney, Agent, or Firm* — Fish & Richardson P.C.

(57) ABSTRACT

A mask apparatus includes a mask body having a fan module, a seal defining a breathing space, a pressure sensor sensing air pressure in the breathing space, a mask body cover coupled to the mask body, and a controller that controls a rotation speed of the fan module based on pressure values. The controller is configured to determine breathing information including a maximum pressure value and time point, and a minimum pressure value and time point, determine a breathing state of a user based on the breathing information, determine whether the breathing state is a steady state, determine a tidal volume of the user based on the breathing information, and control the rotation speed of the fan module based on the tidal volume.

18 Claims, 13 Drawing Sheets

(51) Int. Cl.
*A62B 18/02* (2006.01)
*A62B 18/08* (2006.01)
*A62B 23/02* (2006.01)

(58) Field of Classification Search
CPC ....... A62B 5/087; A62B 5/091; A62B 5/6803; A61M 16/00; A61M 16/0003; A61M 16/0006; A61M 16/0009; A61M 16/0024; A61M 16/0027; A61M 16/003; A61M 16/0033; A61M 16/0036; A61M 16/0039; A61M 16/0057; A61M 16/006; A61M 16/0063; A61M 16/0066; A61M 16/0069; A61M 16/0072; A61M 16/0075; A61M 16/0078; A61M 16/0081; A61M 16/0084

See application file for complete search history.

(56) References Cited

U.S. PATENT DOCUMENTS

| | | | |
|---|---|---|---|
| 5,062,421 A | 11/1991 | Burns et al. | |
| 5,372,130 A | 12/1994 | Stern et al. | |
| 5,782,234 A | 7/1998 | Bates | |
| 6,213,119 B1 | 4/2001 | Brydon et al. | |
| 6,367,470 B1* | 4/2002 | Denyer | B05B 7/0012 |
| | | | 128/200.14 |
| 6,543,450 B1 | 4/2003 | Flynn | |
| 8,667,959 B2 | 3/2014 | Tilley et al. | |
| 10,226,542 B2 | 3/2019 | Messina et al. | |
| 10,342,999 B2 | 7/2019 | Song et al. | |
| 10,661,104 B2 | 5/2020 | Morgan et al. | |
| 11,241,594 B2 | 2/2022 | Szasz et al. | |
| 2003/0052279 A1 | 3/2003 | Kikuchi | |
| 2003/0066257 A1 | 4/2003 | Shovlin | |
| 2003/0066527 A1 | 4/2003 | Chen | |
| 2005/0145249 A1 | 7/2005 | Solyntjes et al. | |
| 2006/0076012 A1 | 4/2006 | Tanizawa et al. | |
| 2007/0125385 A1 | 6/2007 | Ho et al. | |
| 2009/0320847 A1 | 12/2009 | Bozanic et al. | |
| 2010/0101575 A1 | 4/2010 | Fedorko et al. | |
| 2010/0224190 A1 | 9/2010 | Tilley et al. | |
| 2010/0313892 A1 | 12/2010 | Shigematsu et al. | |
| 2010/0329924 A1 | 12/2010 | Harris | |
| 2011/0126713 A1 | 6/2011 | Legare et al. | |
| 2014/0216475 A1 | 8/2014 | Blomberg et al. | |
| 2014/0360501 A1 | 12/2014 | Guiducci et al. | |
| 2015/0034080 A1 | 2/2015 | Furuichi et al. | |
| 2015/0047642 A1 | 2/2015 | Tucker et al. | |
| 2015/0136142 A1 | 5/2015 | Blomberg | |
| 2015/0151143 A1 | 6/2015 | Langford | |
| 2015/0202473 A1 | 7/2015 | Curran et al. | |
| 2015/0217144 A1 | 8/2015 | Skov et al. | |
| 2015/0217146 A1 | 8/2015 | Skov et al. | |
| 2015/0250915 A1 | 9/2015 | Pugh et al. | |
| 2015/0289598 A1 | 10/2015 | Hsiung | |
| 2015/0306324 A1 | 10/2015 | Ayon et al. | |
| 2015/0362478 A1 | 12/2015 | Phillips | |
| 2016/0001111 A1 | 1/2016 | Morgan et al. | |
| 2016/0022944 A1 | 1/2016 | Chodkowski et al. | |
| 2016/0030778 A1 | 2/2016 | Skov et al. | |
| 2016/0030779 A1 | 2/2016 | Twu et al. | |
| 2016/0074604 A1 | 3/2016 | Bronner et al. | |
| 2016/0236016 A1 | 8/2016 | Ono et al. | |
| 2016/0279450 A1 | 9/2016 | Goldstein et al. | |
| 2017/0136271 A1 | 5/2017 | Munster | |
| 2017/0157353 A1 | 6/2017 | Olsen et al. | |
| 2017/0296094 A1* | 10/2017 | Fonzi, III | A61B 5/0002 |
| 2018/0078798 A1 | 3/2018 | Fabian et al. | |
| 2018/0147375 A1* | 5/2018 | Johnson | A61B 5/091 |
| 2018/0177965 A1 | 6/2018 | Patel | |
| 2018/0185677 A1 | 7/2018 | Curran et al. | |
| 2018/0236275 A1 | 8/2018 | Song et al. | |
| 2018/0318457 A1 | 11/2018 | Lucio | |
| 2019/0009114 A1 | 1/2019 | Han | |
| 2019/0113501 A1 | 4/2019 | Jameson et al. | |
| 2019/0160249 A1 | 5/2019 | Rose et al. | |
| 2019/0175962 A1* | 6/2019 | Su | A61M 16/026 |
| 2019/0275357 A1 | 9/2019 | Palmer, Jr. et al. | |
| 2020/0008539 A1 | 1/2020 | Kolasa | |
| 2020/0038614 A1 | 2/2020 | Duff et al. | |
| 2020/0086071 A1 | 3/2020 | Lin et al. | |
| 2020/0087031 A1 | 3/2020 | Yoo et al. | |
| 2020/0129650 A1 | 4/2020 | Kim et al. | |
| 2020/0155877 A1 | 5/2020 | Key et al. | |
| 2021/0085247 A1* | 3/2021 | Meirav | A61B 5/0833 |
| 2021/0228920 A1 | 7/2021 | Arigue et al. | |
| 2021/0337891 A1 | 11/2021 | Shah et al. | |
| 2021/0378325 A1 | 12/2021 | Mun et al. | |
| 2021/0379412 A1 | 12/2021 | Lee et al. | |
| 2021/0379418 A1 | 12/2021 | Kim et al. | |
| 2021/0402222 A1 | 12/2021 | Kwon et al. | |
| 2023/0134274 A1* | 5/2023 | Horwitz | G16H 40/40 |
| | | | 128/204.18 |

FOREIGN PATENT DOCUMENTS

| | | | |
|---|---|---|---|
| CN | 103751919 | | 4/2014 |
| CN | 104162236 | | 11/2014 |
| CN | 203943119 | | 11/2014 |
| CN | 104826247 | | 8/2015 |
| CN | 204637356 | | 9/2015 |
| CN | 105126219 | | 12/2015 |
| CN | 105167366 | | 12/2015 |
| CN | 105476118 | | 4/2016 |
| CN | 105495776 | | 4/2016 |
| CN | 105641821 | | 6/2016 |
| CN | 205285072 | | 6/2016 |
| CN | 106039607 | | 10/2016 |
| CN | 106235464 | | 12/2016 |
| CN | 106253937 | | 12/2016 |
| CN | 106730464 | | 5/2017 |
| CN | 106847663 | | 6/2017 |
| CN | 107149182 | | 9/2017 |
| CN | 206459266 | | 9/2017 |
| CN | 107224687 | | 10/2017 |
| CN | 206577264 | | 10/2017 |
| CN | 107308564 | | 11/2017 |
| CN | 107405508 | | 11/2017 |
| CN | 107735148 | | 2/2018 |
| CN | 206995630 | | 2/2018 |
| CN | 207011751 | | 2/2018 |
| CN | 207040968 | | 2/2018 |
| CN | 207041756 | | 2/2018 |
| CN | 207152901 | | 3/2018 |
| CN | 108126261 | * | 6/2018 |
| CN | 207604526 | | 7/2018 |
| CN | 207721249 | | 8/2018 |
| CN | 207836817 | | 9/2018 |
| CN | 108635689 | | 10/2018 |
| CN | 208145256 | * | 11/2018 |
| CN | 109078277 | | 12/2018 |
| CN | 208403333 | | 1/2019 |
| CN | 208611622 | | 3/2019 |
| CN | 208694061 | | 4/2019 |
| CN | 109924568 | | 6/2019 |
| CN | 111135492 | | 5/2020 |
| CN | 111565763 | | 8/2020 |
| EP | 0558147 | | 9/1993 |
| EP | 0621056 | | 10/1994 |
| EP | 2913083 | | 9/2015 |
| EP | 3406301 A1 | * | 11/2018 ........... A62B 18/006 |
| EP | 3446755 | | 2/2019 |
| EP | 3446756 | | 2/2019 |
| GB | 1155046 | | 6/1969 |
| JP | H05137808 | | 6/1993 |
| JP | 3039303 | | 7/1997 |
| JP | H09225012 | | 9/1997 |
| JP | 10066817 | | 3/1998 |
| JP | H10165527 | | 6/1998 |
| JP | 3077655 | | 5/2001 |
| JP | 2003322712 | | 11/2003 |
| JP | 2004364177 | | 12/2004 |
| JP | 3117209 U | | 1/2006 |
| JP | 2007236600 | | 9/2007 |

(56) References Cited

FOREIGN PATENT DOCUMENTS

| | | |
|---|---|---|
| JP | 2011078604 | 4/2011 |
| JP | 2011078678 | 4/2011 |
| JP | 2011115449 | 6/2011 |
| JP | 2012-075793 | 4/2012 |
| JP | 2013127129 | 6/2013 |
| JP | 3196218 | 2/2015 |
| JP | 2015093036 | 5/2015 |
| JP | 2015-524337 | 8/2015 |
| JP | 2015527130 | 9/2015 |
| JP | 2016087376 | 5/2016 |
| JP | 2018000982 | 1/2018 |
| JP | 2018033905 | 3/2018 |
| JP | 2018089158 | 6/2018 |
| JP | 2018-146805 | 9/2018 |
| JP | 2019501721 | 1/2019 |
| KR | 10-1989-0000137 | 3/1989 |
| KR | 10-1995-0008732 | 8/1995 |
| KR | 20050061384 | 6/2005 |
| KR | 20100081991 | 7/2010 |
| KR | 20-2010-0009804 | 10/2010 |
| KR | 1020110067854 | 6/2011 |
| KR | 20120051735 | 5/2012 |
| KR | 200461294 | 7/2012 |
| KR | 101228403 | 1/2013 |
| KR | 101536265 | 7/2015 |
| KR | 101554664 | 9/2015 |
| KR | 101619487 | 5/2016 |
| KR | 20160062808 | 6/2016 |
| KR | 20160129562 | 11/2016 |
| KR | 20160132159 | 11/2016 |
| KR | 101733470 | 4/2017 |
| KR | 20170111132 | 10/2017 |
| KR | 20170126163 | 11/2017 |
| KR | 20180009326 | 1/2018 |
| KR | 10-2018-0012496 | 2/2018 |
| KR | 101827016 | 2/2018 |
| KR | 1020180027561 | 3/2018 |
| KR | 101849610 | 4/2018 |
| KR | 20180043234 | 4/2018 |
| KR | 20180045934 | 5/2018 |
| KR | 20180064284 | 6/2018 |
| KR | 20180091698 | 8/2018 |
| KR | 20180128040 | 11/2018 |
| KR | 10-2018-0130658 | 12/2018 |
| KR | 101925388 | 12/2018 |
| KR | 1020180135840 | 12/2018 |
| KR | 10-1942785 | 1/2019 |
| KR | 20190033299 | 3/2019 |
| KR | 1020190033299 | 3/2019 |
| KR | 10-2019-0053757 | 5/2019 |
| KR | 10-2019-0022668 | 6/2019 |
| KR | 102002878 | 7/2019 |
| KR | 1020190089188 | 7/2019 |
| KR | 20190100605 | 8/2019 |
| KR | 1020190096496 | 8/2019 |
| KR | 102023974 | 9/2019 |
| KR | 10-2019-0119804 | 10/2019 |
| KR | 101997813 | 10/2019 |
| KR | 102065360 | 2/2020 |
| KR | 1020200033495 | 3/2020 |
| KR | 102110687 | 5/2020 |
| KR | 20200048502 | 5/2020 |
| KR | 1020200048502 | 5/2020 |
| KR | 1020200049490 | 5/2020 |
| KR | 1020200079925 | 7/2020 |
| TW | 201201879 | 1/2012 |
| TW | M555232 | 2/2018 |
| TW | 201904614 | 2/2019 |
| WO | WO 1996/22124 | 7/1996 |
| WO | WO2009067583 | 5/2009 |
| WO | WO2010070495 | 6/2010 |
| WO | WO2014020469 | 2/2014 |
| WO | WO 2016/072868 | 5/2016 |
| WO | WO2016157159 | 10/2016 |
| WO | WO20170004313 | 1/2017 |
| WO | WO2017116174 | 7/2017 |
| WO | WO2018036902 | 3/2018 |
| WO | WO2018147941 | 8/2018 |
| WO | WO-2019025340 A1 * | 2/2019 ............ A62B 18/00 |
| WO | WO 2019/059699 | 3/2019 |
| WO | WO2020055106 | 3/2020 |
| WO | WO2020094850 | 5/2020 |

OTHER PUBLICATIONS

Extended European Search Report in European Appln. No. 21169777.6, dated Sep. 24, 2021, 5 pages.
Extended European Search Report in European Appln. No. 20217533.7, dated Jun. 8, 2021, 5 pages.
Office Action in Chinese Appln. No. 202011089763, mailed on Feb. 11, 2023, 18 pages (with English translation).
Office Action in Chinese Appln. No. 202011328031, mailed on Feb. 15, 2023, 18 pages (with English translation).
Office Action in Chinese Appln. No. 202110184702, mailed on Mar. 18, 2023, 23 pages (with English translation).
Office Action in Korean Appln. No. 20210129533, mailed on Mar. 28, 2023, 18 pages (with English translation).
Office Action in Korean Appln. No. 20220126062, mailed on Mar. 23, 2023, 23 pages (with English translation).
Office Action in U.S. Appl. No. 17/170,035, mailed on Feb. 8, 2023, 8 pages.
Office Action in U.S. Appl. No. 17/178,103, mailed on Jun. 30, 2023, 30 pages.
Office Action in Taiwanese Appln. No. 11120021940, dated Dec. 20, 2020, 11 pages (with English translation).
Notice of Allowance in Korean Appln. No. 10-2020-0068407, dated Nov. 29, 2021, 4 pages (with English translation).
Office Action in Korean Appln. No. 10-2020-0068400, dated Dec. 27, 2021, 13 pages (with English translation).
Office Action in Korean Appln. No. 10-2020-0068412, dated Dec. 27, 2021, 15 pages (with English translation).
Office Action in Korean Appln. No. 10-2020-0080417, dated Dec. 28, 2021, 13 pages (with English translation).
Office Action in Korean Appln. No. 10-2020-0089132, dated Dec. 28, 2021, 13 pages (with English translation).
Office Action in Korean Appln. No. 10-2020-0068413, dated Nov. 17, 2021, 13 pages (with English translation).
Office Action in Korean Appln. No. 10-2020-0080087, dated Nov. 30, 2021, 15 pages (with English translation).
Office Action in Indian Appln. No. 202114007027, dated Jan. 5, 2022, 6 pages.
Office Action in Indian Appln. No. 202114003123, dated Jan. 6, 2022, 5 pages.
Office Action in Indian Appln. No. 202114008985, dated Jan. 12, 2022, 5 pages.
Office Action in Indian Appln. No. 202114003125, dated Jan. 13, 2022, 5 pages.
Office Action in Indian Appln. No. 202114007372, dated Jan. 24, 2022, 6 pages.
Notice of Allowance in Korean Appln. No. 10-2020-0068413, dated May 31, 2022, 4 pages (with English translation).
Notice of Allowance in Korean Appln. No. 10-2020-0080087, dated Jun. 30, 2022, 5 pages (with English translation).
Office Action in Chinese Appln. No. 202011328161.5, dated Apr. 2, 2022, 15 pages (with English translation).
Office Action in Chinese Appln. No. 202110046911.8, dated Apr. 15, 2022, 12 pages (with English translation).
Office Action in Chinese Appln. No. 202110382635.2, dated Apr. 20, 2022, 12 pages (with English translation).
Office Action in Chinese Appln. No. 202110383659.X, dated Apr. 18, 2022, 13 pages (with English translation).
Office Action in Chinese Appln. No. 202110404827.9, dated Apr. 19, 2022, 13 pages (with English translation).
Office Action in Japanese Appln. No. 2021-043251, dated May 10, 2022, 6 pages (with English translation).
Office Action in Japanese Appln. No. 2021-073811, dated May 10, 2022, 6 pages (with English translation).

(56) References Cited

OTHER PUBLICATIONS

Office Action in Japanese Appln. No. 2021-074825, dated Apr. 19, 2022, 6 pages (with English translation).
Office Action in Japanese Appln. No. 2021-090930, dated Jun. 14, 2022, 10 pages (with English translation).
Office Action in Chinese Appln. No. 202011403700.7, dated May 4, 2023, 18 pages (with English translation).
Office Action in Chinese Appln. No. 202110096186.5, dated Jun. 3, 2023, 16 pages (with English translation).
Office Action in U.S. Appl. No. 17/230,206, dated Jun. 22, 2023, 18 pages.
Office Action in U.S. Appl. No. 17/231,472, dated Jun. 23, 2023, 23 pages.
Notice of Allowance in Japanese Appln. No. 2020-204668, dated Aug. 16, 2022, 5 pages (with English translation).
Office Action in Chinese Appln. No. 202110552518.6, dated Jul. 4, 2022, 18 pages (with English translation).
Korean Office Action in Korean Appln. No. 10-2020-0068402, dated Oct. 15, 2020, 20 pages (with English translation).
Office Action in Japanese Appln. No. 2020-204668, dated Feb. 7, 2022, 12 pages (with English translation).
Office Action in Korean Appln. No. 10-2020-0080437, dated Feb. 21, 2022, 13 pages (with English translation).
Office Action in Korean Appln. No. 10-2020-0068421, dated Jan. 23, 2022, 12 pages (with English translation).
Office Action in Chinese Appln. No. 202110096186.5, mailed on Feb. 9, 2024, 7 pages (with English translation).
Office Action in U.S. Appl. No. 17/121,056, mailed on Dec. 21, 2023, 10 pages.
Office Action in U.S. Appl. No. 17/121,115, mailed on Dec. 20, 2023, 11 pages.
Office Action in U.S. Appl. No. 17/174,766, mailed on Dec. 5, 2023, 12 pages.
Office Action in U.S. Appl. No. 17/231,462, mailed on Dec. 28, 2023, 17 pages.
Office Action in U.S. Appl. No. 17/231,472, mailed on Feb. 27, 2024, 20 pages.
Office Action in U.S. Appl. No. 17/244,683, mailed on Feb. 8, 2024, 14 pages.
Extended European Search Report in European Appln. No. 20217535.2, dated Jun. 22, 2021, 4 pages.
Extended European Search Report in European Appln. No. 20217537.8, dated Jun. 22, 2021, 4 pages.
Office Action in Korean Appln. No. 10-2020-0068404, dated Jun. 30, 2021, 12 pages (with English translation).
Office Action in Korean Appln. No. 10-2020-0068611, dated Jun. 30, 2021, 12 pages (with English translation).
Office Action in Taiwanese Appln. No. 109146705, dated Jul. 7, 2021, 19 pages (with English translation).
Office Action in Taiwanese Appln. No. 110102539, dated Jul. 12, 2021, 10 pages (with English translation).
Office Action in Taiwanese Appln. No. 110102540, dated Jul. 12, 2021, 19 pages (with English translation).
Office Action in Taiwanese Appln. No. 110105039, dated Jul. 12, 2021, 15 pages (with English translation).
Notice of Allowance in U.S. Appl. No. 17/178,103, mailed on Nov. 3, 2023, 12 pages.
Office Action in Korean Appln. No. 10-2022-0126062, mailed on Sep. 26, 2023, 8 pages (with English translation).
Office Action in U.S. Appl. No. 17/112,500, mailed on Nov. 28, 2023, 14 pages.
Office Action in U.S. Appl. No. 17/230,206, mailed on Oct. 12, 2023, 19 pages.
Office Action in U.S. Appl. No. 17/231,472, mailed on Oct. 23, 2023, 19 pages.
Office Action in U.S. Appl. No. 17/244,683, mailed on Oct. 13, 2023, 21 pages.
Decision to Grant a Patent in Japanese Appln. No. 2021-043251, dated Oct. 25, 2022, 5 pages (with English translation).
Office Action in European Appln. No. 20217533.7, dated Nov. 23, 2022, 5 pages.
Office Action in European Appln. No. 21182279.6, dated Oct. 17, 2022, 2 pages.
Office Action in Taiwanese Appln. No. 110117972, dated Oct. 7, 2022, 14 pages (with English translation).
Office Action in U.S. Appl. No. 17/170,035, dated Sep. 29, 2022, 19 pages.
Written Decision on Registration in Korean Appln. No. 10-2020-0080437, dated Oct. 22, 2022, 11 pages (with English translation).
Extended European Search Report in European Appln. No. 21169778.4, dated Oct. 15, 2021, 5 pages.
Extended European Search Report in European Appln. No. 21169793.3, dated Oct. 15, 2021, 4 pages.
Extended European Search Report in European Appln. No. 21169796.6, dated Oct. 18, 2021, 4 pages.
Extended European Search Report in European Appln. No. 21169813.9, dated Oct. 20, 2021, 4 pages.
Extended European Search Report in European Appln. No. 21169817.0, dated Oct. 14, 2021, 4 pages.
Extended European Search Report in European Appln. No. 21170476.2, dated Oct. 13, 2021, 4 pages.
Extended European Search Report in European Appln. No. 21170861.5, dated Oct. 25, 2021, 4 pages.

\* cited by examiner

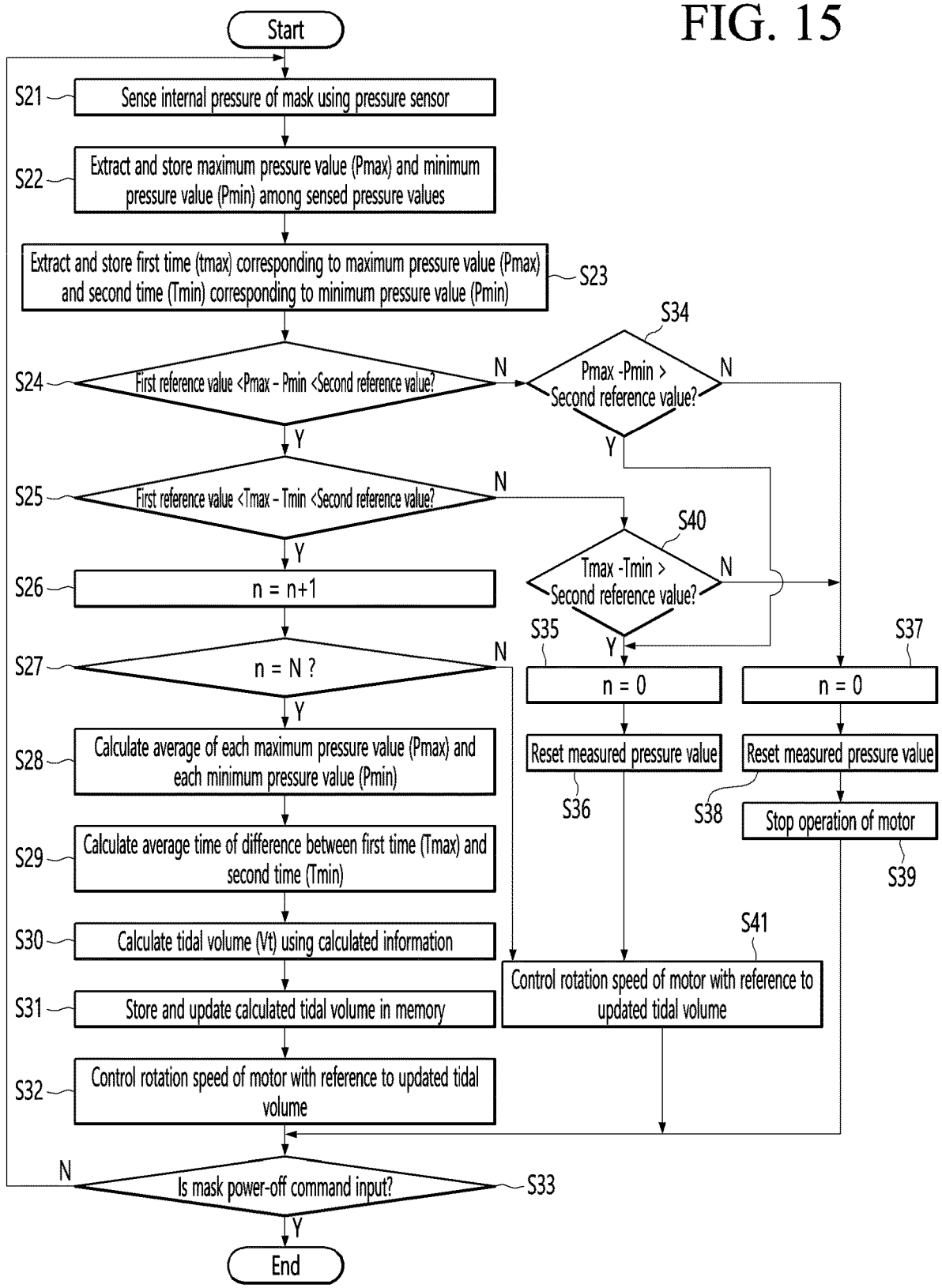

MASK APPARATUS AND METHOD FOR CONTROLLING THE SAME

CROSS-REFERENCE TO RELATED APPLICATIONS

The present application claims the benefits of priority to Korean Patent Application No. 10-2020-0089132, filed on Jul. 17, 2020, the disclosures of which are incorporated herein by reference in their entireties.

TECHNICAL FIELD

The present disclosure relates to a mask apparatus and a method for controlling the same.

BACKGROUND

A mask is a device that can cover a user's nose and mouth to reduce or prevent inhalation of germs and dust or droplet transmitting viruses or bacteria. The mask can be in close contact with the user's face to cover the user's nose and mouth. The mask can filter germs, dust, and the like, which may be contained in the air, and provide the filtered air to the user's mouth and nose. Air containing germs and dust may pass through a body of the mask including a filter configured to block the germs and the dust.

In some cases, the mask can cause an uncomfortable breathing since air is introduced into the user's nose and mouth and discharged to the outside after passing through the body of the mask.

In some cases, a mask can include a motor, a fan, and a filter. For example, an electric dust mask can include a mask body, a filter formed on the mask body, a motor controlling a flow rate of air introduced through the filter, and a differential sensor measuring a pressure change inside the mask body.

In some cases, where a plurality of differential pressure sensors for respectively measuring internal and external pressures of the mask are installed for recognizing the user's breath, manufacturing cost of the mask can increase.

In some cases, whether the user breathes or talks are determined using the pressure difference between the inside and outside of the mask, and accordingly, an output of the motor may be constantly controlled, but the user's breathing state is not specifically considered.

In some cases, since there is a breathing deviation according to the individual difference of the user, a fan may not be optimally controlled.

In some cases, the surrounding environment suddenly changes (e.g., a situation in which an air pressure is changed by getting on an elevator), it may be difficult to accurately determine the breathing state. If the breathing state is not accurately determined, the breathing may become uncomfortable due to improper operation of the fan.

SUMMARY

The present disclosure describes a mask apparatus that can accurately control a fan according to determination of a user's breathing pattern or breathing cycle, and a method for controlling the same.

The present disclosure also describes a mask apparatus that can determine user's exercise intensity in consideration of a user's breathing pattern and adequately adjust a rotational speed of a fan according to the determined exercise intensity, and a method for controlling the same.

The present disclosure further describes a mask apparatus including a fan controlled in consideration of a situation in which surrounding environment is changed rapidly to facilitate breathing, and a method for controlling the same.

According to one aspect of the subject matter descried in this application, a mask apparatus includes a mask body configured to mount a fan module, a seal coupled to a rear surface of the mask body, where the seal is configured to define a breathing space therein, a pressure sensor coupled to the mask body and configured to sense air pressure in the breathing space, a mask body cover that is coupled to a front surface of the mask body and covers the fan module, and a controller coupled to the mask body and configured to control a rotation speed of the fan module based on pressure values measured by the pressure sensor. The controller is configured to determine breathing information including a maximum pressure value and a minimum pressure value among the pressure values, a maximum time point corresponding to the maximum pressure value, and a minimum time point corresponding to the minimum pressure value. The controller is configured to determine a breathing state of a user based on the breathing information, determine whether the breathing state is a steady state, determine a tidal volume of the user based on the breathing information, where the tidal volume represents a volume of air that the user breathes in and out in the steady state, and control the rotation speed of the fan module based on the tidal volume.

Implementations according to this aspect can include one or more of the following features. For example, the controller can be configured to determine a difference value between the maximum pressure value and the minimum pressure value, compare the difference value to a reference value, and determine the breathing state based on comparing the difference value to the reference value. In some examples, the reference value can include a first reference value, and a second reference value greater than the first reference value, where wherein the controller is configured to determine that the breathing state is the steady state based on the difference value being greater than the first reference value and less than the second reference value.

In some implementations, the controller is configured to determine a time difference between the maximum time point and the minimum time point, compare the time difference to a reference time, and determine the breathing state based on comparing the time difference to the reference time. In some examples, the reference time includes a first reference duration, and a second reference duration greater than the first reference duration, where the controller is configured to determine that the breathing state is the steady state based on the time difference being greater than the first reference duration and less than the second reference duration.

In some examples, the controller is configured to, based on determining that the breathing state is the steady state, determine the tidal volume by using the difference value and the time difference. In some examples, the controller is configured to determine a breathing volume per unit time that is defined by dividing the tidal volume by the time difference, and control the rotation speed of the fan module based on the breathing volume per unit time.

In some examples, the controller is configured to determine (i) a mean maximum pressure value of a plurality of maximum pressure values sensed during the steady state, (ii) a mean minimum value of a plurality of minimum pressure values sensed during the steady state, and (iii) a mean time difference determined based on a plurality of time differences, wherein each time difference corresponds to a difference between time points corresponding to one of the plurality of maximum pressure values and one of the plurality of minimum pressure values. The controller can be configured to determine the tidal volume based on the mean maximum pressure value, the mean minimum value, and the mean time difference.

In some implementations, the controller is configured to store information of the tidal volume in a non-transitory memory, update the information of the tidal volume, and control the rotation speed of the fan module based on the updated information of the tidal volume. In some examples, the controller is configured to, based on the difference value being greater than the second reference value, determine that the breathing state is an exercise state, and, based on determining that the breathing state is the exercise state, reset the measured pressure values and control the rotation speed of the fan module based on tidal volume data stored before the breathing state is the exercise state.

In some implementations, the controller is configured to, based on the difference value being less than the first reference value, determine that the mask apparatus is not worn by the user, and, based on determining that the mask apparatus is not worn by the user, reset the measured pressure values and stop operation of the fan module.

In some implementations, the controller is configured to, based on the time difference being greater than the second reference duration, determine that the user is in a deep breathing state, and, based on determining that the user is in the deep breathing state, reset the measured pressure values and control the rotation speed of the fan module based on tidal volume data stored before the user is in the deep breathing state.

In some implementations, the controller is configured to, based on the time difference being less than the first reference duration, determine that the user is in an abnormal breathing state or that the mask apparatus is in a malfunction state, and based on determining that the user is in the abnormal breathing state or that the mask apparatus is in the malfunction state, reset the measured pressure values and stop operation of the fan module.

According to another aspect, a method for controlling a mask apparatus includes sensing an internal pressure of the mask apparatus by a pressure sensor, and determining breathing information including a maximum pressure value and a minimum pressure value among pressure values measured by the pressure sensor, a maximum time point corresponding to the maximum pressure value, and a minimum time point corresponding to the minimum pressure value. The method further includes storing the breathing information, determining a breathing state of a user based on the breathing information, determining whether the breathing state is a steady state, determining a tidal volume of the user based on the breathing information, where the tidal volume represents a volume of air that the user breathes in and out when the breathing state is the steady state, and controlling a rotation speed of a fan module of the mask apparatus based on the tidal volume.

Implementations according to this aspect can include one or more of the following features. For example, determining the breathing state can include determining a difference value between the maximum pressure value and the minimum pressure value, comparing the difference value to a reference value, determining the breathing state based on comparing the difference value to the reference value, where the reference value includes a first reference value and a second reference value greater than the first reference value, and determining that the breathing state is the steady state based on the difference value being greater than the first reference value and less than the second reference value.

In some implementations, determining the breathing state can include determining a time difference between the maximum time point and the minimum time point, comparing the time difference to a reference time, determining the breathing state based on comparing the time difference to the reference time, where the reference time includes a first reference duration and a second reference duration greater than the first reference duration, and determining that the breathing state is the steady state based on the time difference being greater than the first reference duration and less than the second reference duration.

In some examples, determining the tidal volume includes calculating an equation that has the difference value and the time difference as variables, and controlling the rotation speed of the fan module includes determining a breathing volume per unit time that is defined by dividing the tidal volume by the time difference, and controlling the rotation speed of the fan module based on the breathing volume per unit time.

In some examples, determining the breathing information can include determining (i) a mean maximum pressure value of a plurality of maximum pressure values sensed during the steady state, (ii) a mean minimum value of a plurality of minimum pressure values sensed during the steady state, and (iii) a mean time difference determined based on a plurality of time differences, wherein each time difference corresponds to a difference between time points corresponding to one of the plurality of maximum pressure values and one of the plurality of minimum pressure values.

In some implementations, the method can include storing information of the tidal volume in a non-transitory memory, and updating the information of the tidal volume, where controlling the rotation speed of the fan module includes controlling the rotation speed of the fan module based on the updated information of the tidal volume.

In some implementations, determining the breathing state can include determining that the breathing state is an exercise state based on the difference value being greater than the second reference value. The method can further include resetting the measured pressure values based on determining that the breathing state is the exercise state, where controlling the rotation speed of the fan module can include controlling the rotation speed of the fan module based on tidal volume data stored before the breathing state is the exercise state.

In some implementations, the method can include, based on the difference value being less than the first reference value, determining that the mask apparatus is not worn by the user, and, based on determining that the mask apparatus is not worn by the user, resetting the measured pressure values and stopping operation of the fan module.

In some implementations, the method can include, based on the time difference being greater than the second reference duration, determining that the user is in a deep breathing state, and, based on determining that the user is in the deep breathing state, resetting the measured pressure values and controlling the rotation speed of the fan module based on tidal volume data stored before the user is in the deep breathing state.

In some implementations, the method can include, based on the time difference being less than the first reference duration, determining that the user is in an abnormal breathing state or that the mask apparatus is in a malfunction state, and, based on determining that the user is in the abnormal breathing state or that the mask apparatus is in the malfunction state, resetting the measured pressure values and stopping operation of the fan module.

In some implementations, the user's breathing states (stable state, exercise state, and abnormal state) can be determined according to the internal pressure of the mask, and the appropriate motor control can be performed according to the determined breathing state to facilitate the breathing.

For example, since the user's breathing pattern or breathing cycle is determined through the pressure values sensed in the stable state, the inhalation time, and the tidal volume, the reliability of the mask can be improved.

In some implementations, since the tidal volume stored in the memory is periodically updated and reflected, the fan control according to the breathing deviation of each user can be precisely performed.

In some implementations, the appropriate operations can be performed by determining not only the user's exercise state, but also the external environment changes or malfunctions of the machine, and thus the user convenience can be improved.

In some implementations, the breathing state can be determined by using the single pressure sensor, and the motor can be controlled according to the breathing state. Thus, the structure can be simplified, and the product cost can be reduced.

BRIEF DESCRIPTION OF THE DRAWINGS

FIG. 15 is a detailed flowchart illustrating an example of a method for controlling a mask apparatus.

DETAILED DESCRIPTION

Figure 1:
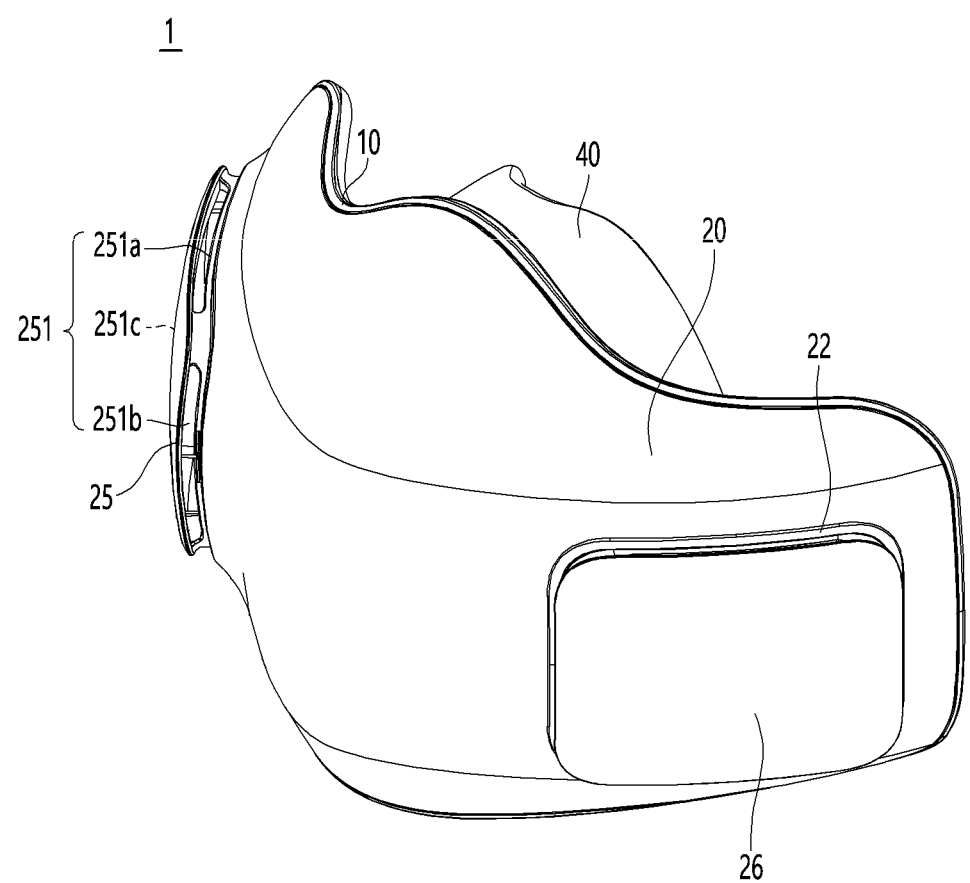
FIG. 1 is a left perspective view showing an example of a mask apparatus.
Figure 2:
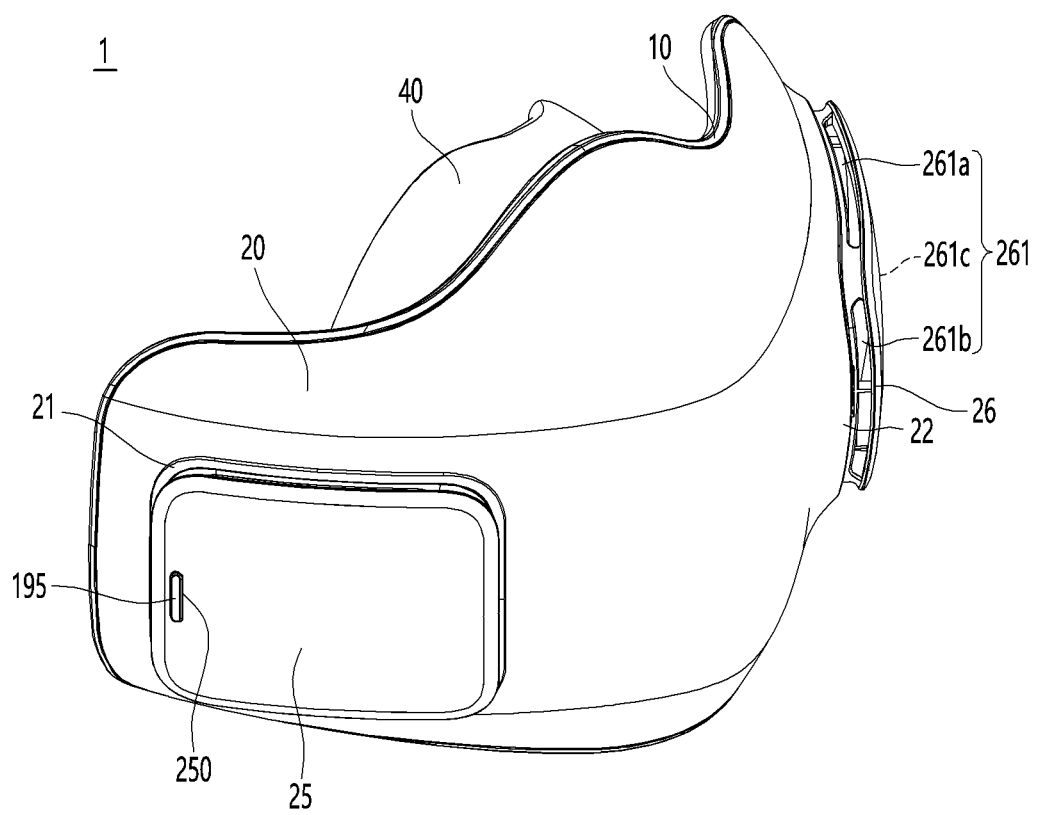
FIG. 2 is a right perspective view showing the mask apparatus.
Figure 3:
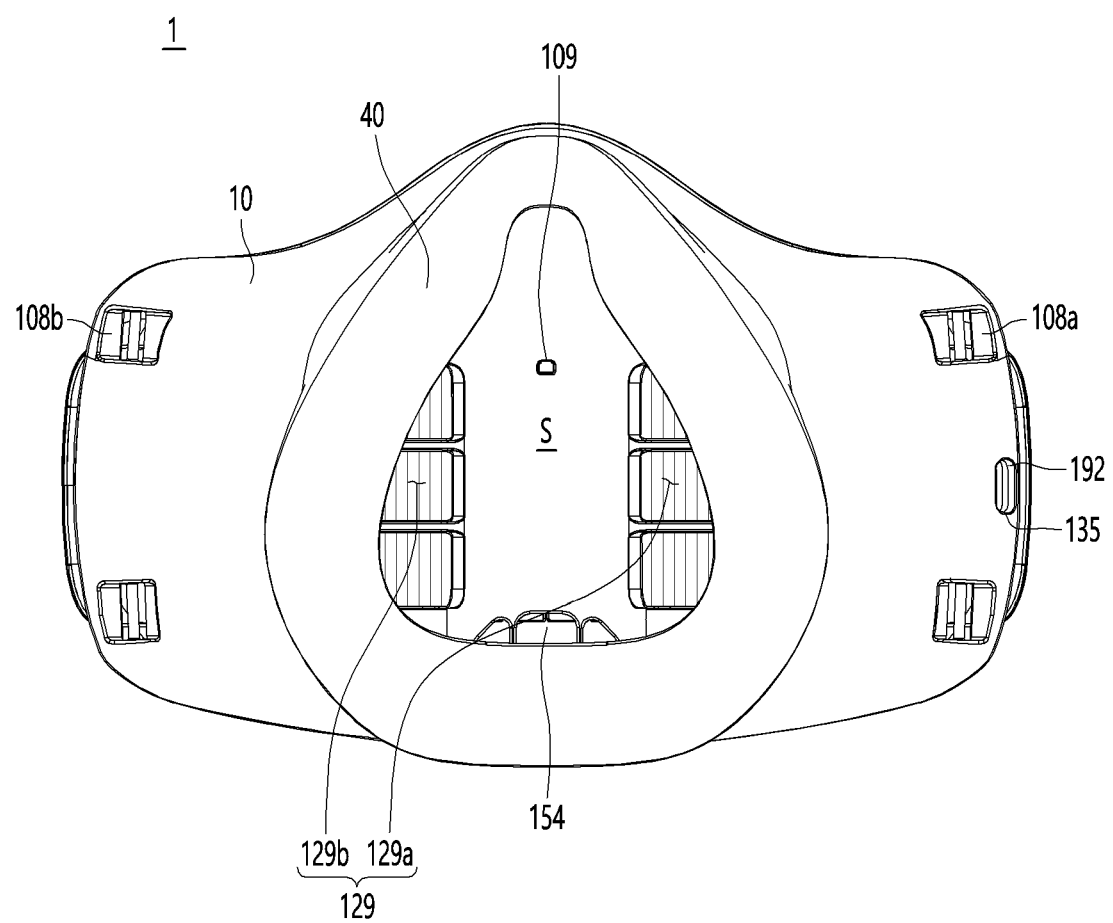
FIG. 3 is a rear view showing the mask apparatus.
Figure 4:
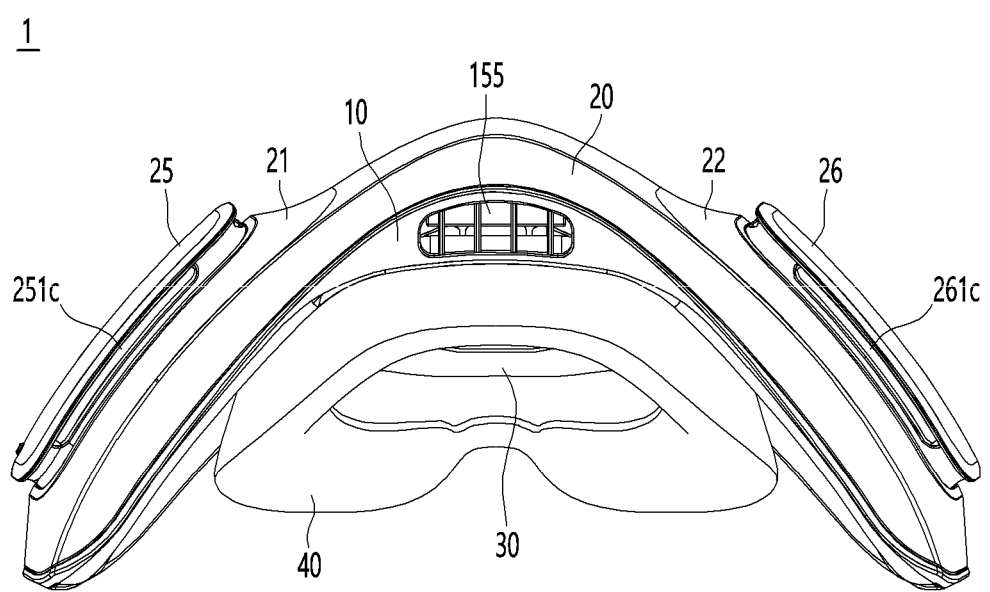
FIG. 4 is a bottom view showing the mask apparatus.

FIG. 1 is a left perspective view showing an example of a mask apparatus, FIG. 2 is a right perspective view showing the mask apparatus, FIG. 3 is a rear view showing the mask apparatus, and FIG. 4 is a bottom view showing the mask apparatus.

Referring to FIGS. 1 to 4, a mask apparatus 1 can include a mask body 10 and a mask body cover 20 coupled to the mask body 10.

The mask body 10 and the mask body cover 20 can be detachably coupled to each other. When the mask body 10 and the mask body cover 20 are coupled to each other, an inner space can be defined between the mask body 10 and the mask body cover 20. Constituents for driving the mask apparatus 1 can be disposed in the inner space. The inner space can be defined between a front surface of the mask body 10 and a rear surface of the mask body cover 20. The mask body 10 can define a rear surface of the mask apparatus 1, and the mask body cover 20 can define a front surface of the mask apparatus 1.

A rear side of the mask apparatus 1 is defined as a direction in which the rear surface of the mask apparatus 1 facing a user's face is disposed, and a front side of the mask apparatus 1 is defined as a direction which is opposite to the rear side and in which a front surface of the mask apparatus 1, which is exposed to the outside, is disposed.

The mask apparatus 1 can further include a sealing bracket 30 and a seal 40 that is detachably coupled to the sealing bracket 30.

The sealing bracket 30 can be detachably coupled to a rear surface of the mask body 10 to fix the seal 40 to the rear surface of the mask body 10. In some implementations, when the sealing bracket 30 is separated from the rear surface of the mask body 10, the seal 40 can be separated from the mask body 10.

The seal 40 can be supported on the rear surface of the mask body 10 by the sealing bracket 30, and a breathing space S for breathing can be defined between the seal 40 and the rear surface of the mask body 10. The seal 40 can be in close contact with a user's face and can surround user's nose and mouth to restrict introduction of external air into the breathing space S.

The mask body cover 20 can include a first filter mounting portion 21 and a second filter mounting portion 22. The first filter mounting portion 21 can be disposed at a right side of the mask body cover 20, and the second filter mounting portion 22 can be disposed at a left side of the mask body cover 20.

A left direction (left side) and a right direction (right side) are defined based on the mask apparatus 1 worn on the user's face. That is, in the state in which the user wearing the mask apparatus 1, a right side of the user is defined as the right side of the mask apparatus 1, and a left side of the user is defined as the left side of the mask apparatus 1.

In some implementations, an upward direction (upward side) and a downward direction (downward side) are defined based on the mask apparatus 1 mounted on the user's face.

A first filter cover 25 can be mounted on the first filter mounting portion 21, and a second filter cover 26 can be mounted on the second filter mounting portion 22. Filters 23 and (see FIG. 5) can be disposed inside the first filter mounting portion 21 and the second filter mounting portion 22, and the first filter cover 25 and the second filter cover 26 can cover the filter.

The first filter cover 25 and the second filter cover 26 can be detachably coupled to the first filter mounting portion 21 and the second filter mounting portion 22, respectively. For example, the first filter cover 25 and the second filter cover 26 can be coupled to be fitted into the first filter mounting portion 21 and the second filter mounting portion 22, respectively.

Each of the first filter cover 25 and the second filter cover 26 can include a front surface portion and side surface portions extending backward along an edge of the front surface portion or an edge of a rear surface.

Each of the side surface portions of the first filter cover 25 and the second filter cover 26 can have four side surfaces, and the four side surfaces can include an upper side surface, a lower side surface, a left side surface, and a right side surface.

One or a plurality of first air inlets 251 can be defined in the side surface portion of the first filter cover 25. One or a plurality of second air inlets 261 can also be defined in the side surface portion of the second filter cover 26.

In the state in which the first filter cover 25 is mounted on the first filter mounting portion 21, the first air inlet 251 can be defined to be exposed to the outside. In the state in which the second filter cover 26 is mounted on the second filter mounting portion 22, the second air inlet 261 can be defined to be exposed to the outside.

The first air inlet 251 and the second air inlet 261 can be defined in the side surfaces of the first filter cover 25 and the second filter cover 26, respectively. In some implementations, each of the first and second air inlets 251 and 261 are respectively defined in the front surface portions of the first and second filter covers 25 and 26.

The first air inlet 251 and the second air inlet 261 can be defined at a point closer to the front surface portion from a line that bisects the side surface portion.

When a plurality of the first air inlets 251 are provided in the side surface portions of the first filter cover 25, the first air inlets 251 can include a first air suction hole 251a defined in the right side surface, a second air suction hole 251b defined in the left side surface, and a third air suction hole 251c defined in the upper side surface.

Similarly, when a plurality of the second air inlets 261 are provided in the side surface portions of the second filter cover 26, the second air inlets 261 can include a first air suction hole 261a defined in the left side surface, a second air suction hole 261b defined in the right side surface, and a third air suction hole 261c defined in the upper side surface.

An opening 250 can be defined in one of the first filter cover 25 and the second filter cover 26, and the opening 250 can be defined in an edge of one of the first filter cover 25 and the second filter cover 26. In some implementations, a manipulation portion 195 for controlling an operation of the mask apparatus 1 can be mounted in the opening 250. In some examples, the manipulation portion 195 is mounted on the first filter cover 25 as an example.

The manipulation portion 195 can serve as a manipulation switch that turns on/off power of the mask apparatus 1. The manipulation portion 195 can be exposed to the front side of the mask apparatus 1 while being mounted in the opening 250.

The mask body 10 can include a hook mounting portion 108. The hook mounting portion 108 can be provided on the left and right sides of the mask body 10.

That is, the hook mounting portion 108 can include a first hook mounting portion 108a provided at a right side of the mask body 10, and a second hook mounting portion 108b provided at a left side of the mask body 10.

Each of the first hook mounting portion 108a and the second hook mounting portion 108b can be provided in plurality to be spaced apart from each other in a vertical direction of the mask body 10. In detail, the first hook mounting portion 108a can be provided at each of the upper right and lower right sides of the mask body 10, and the second hook mounting portion 108b can be provided at each of the upper left and lower left sides of the mask body 10.

Bands for maintaining the mask apparatus 1 in close contact with the user's face can be coupled to the hook mounting portion 108.

For example, both ends of each of the bands can connect the first hook mounting portion 108a to the second hook mounting portion 108b, or two bands can respectively connect two first hook mounting portions 108a spaced apart from each other in the vertical direction to two second hook mounting portions 108b spaced apart from each other in the vertical direction to each other.

In the former case, the band can have a shape surrounding the user's occipital region, and in the latter case, the band can have a shape that is hooked on both ears of the user.

The hook mounting portion 108 can be formed by cutting a portion of the mask body 10. Thus, air can be introduced into the inner space between the mask body 10 and the mask body cover 20 through a gap defined in the hook mounting portion 108.

In detail, the external air introduced into the inner space through the hook mounting portion 108 can cool electronic components disposed in the inner space. In some implementations, the air of which a temperature increases while cooling the electronic components can be discharged again to the outside of the mask body 10 through the hook mounting portion 108. In some implementations, to restrict a flow of the air introduced into the inner space through the hook mounting portion 108 into the breathing space, the inside of the mask apparatus 1 can have a sealing structure.

The mask body 10 can include an air outlet 129 for supplying the filtered air to the breathing space. The user can breathe while breathing the filtered air supplied through the air outlet 129 to the breathing space.

The air outlet 129 can include a first air outlet 129a through which the filtered air introduced into the first air inlet 251 is discharged to the breathing space S and a second air outlet 129b through which the filtered air introduced into the second air inlet 261 is discharged to the breathing space S.

The first air outlet 129a can be defined at a right side with respect to a center of the mask body 10, and the second air outlet 129b can be defined at a left side with respect to the center of the mask body 10. The air introduced through the first air inlet 251 can pass through the filter 23 and then flow to the first air outlet 129a. The air introduced through the second air inlet 261 can pass through the filter 24 and then flow to the second air outlet 129b.

The mask body 10 can include air exhaust holes 154 and 155 for discharging air exhaled by the user to an external space. The air exhaust holes 154 and 155 can be defined in a lower portion the mask body 10.

The air exhaust holes 154 and 155 can include a first air exhaust hole 154 defined in a front lower end of the mask body 10 and a second air exhaust hole 155 defined in a bottom surface of the mask body 10.

In detail, a rib extending forward can be formed at the front lower end of the mask body 10, and a surface defined by the rib can be defined as the bottom surface of the mask body 10.

A flow space through the air flowing toward the second air exhaust hole 155 by passing through the first air exhaust hole 154 descends can be defined between the mask body 10 and the mask body cover 20.

A check valve can be provided in one or more of the first air exhaust hole 154 and the second air exhaust hole 155. The external air can be introduced into the breathing space, or the air discharged through the second air exhaust hole 155 can be prevented from flow backward by the check valve.

The check valve can be disposed in the flow space between the first air exhaust hole 154 to the second air exhaust hole 155.

For example, the check valve in a form of a flat flap having a size and shape corresponding to the size and shape of the first air exhaust hole 154 can be provided.

In detail, an upper end of the flap can be connected to an upper edge of the first air exhaust hole 154, and when the user exhales, the flap can be bent or rotate to open the first air exhaust hole 154, and when the user inhales, the flap can be in close contact with the first air exhaust hole 154 to prevent the external air or the discharged air from being introduced again into the breathing space.

The mask body 10 can include a sensor mounting portion 109. The sensor mounting portion 109 can be equipped with a sensor for acquiring various pieces of information from the breathing space. The sensor mounting portion 109 can be disposed above the mask body 10. When the user breathes, the sensor mounting portion 109 can be disposed above the mask body 10 in consideration of a position at which a pressure change in the breathing space is constantly sensed.

The mask body 10 can include a connector hole 135. The connector hole 135 can be understood as an opening in which a connector 192 for supplying power to the mask apparatus 1 is installed. The connector hole 135 can be defined at either a left edge or a right edge of the mask body 10.

In some examples, since the manipulation portion 195 and the connector 192 are connected to a power module 19 (see FIG. 5) to be described later, the connector hole 135 can be provided at one side of the left or the right side of the mask body 10, which corresponds to the position at which the power module 19 is installed.

Hereinafter, constituents of the mask apparatus 1 will be described in detail based on an exploded perspective view.

Figure 5:
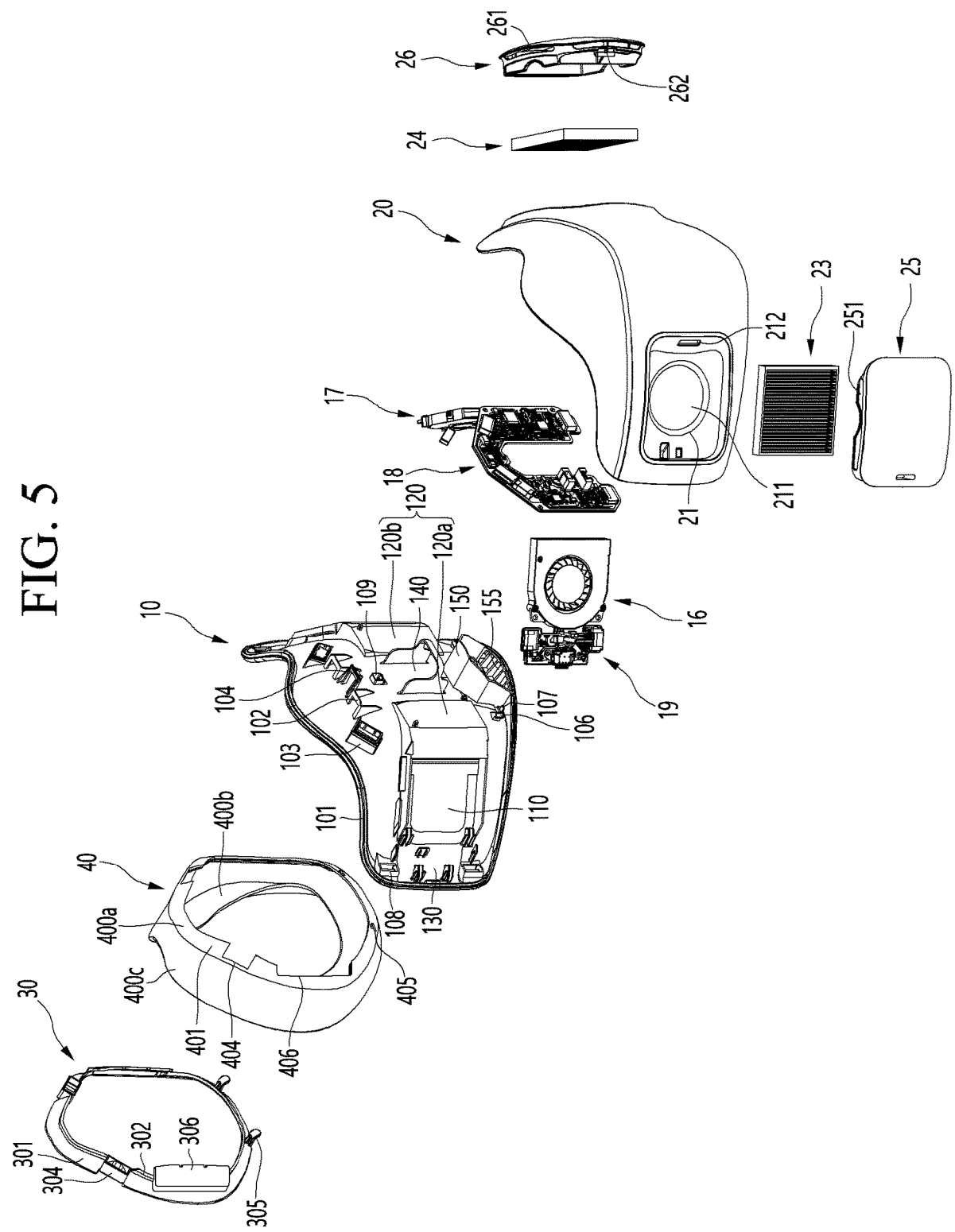
FIG. 5 is an exploded perspective view showing the mask apparatus.

FIG. 5 is an exploded perspective view showing the mask apparatus.

Referring to FIG. 5, the mask apparatus 1 can include the mask body 10, the mask body cover 20, the sealing bracket 30, and the seal 40.

In some implementations, the mask body 10 and the mask body cover 20 can be coupled to each other to form an outer appearance of the mask apparatus 1.

An inner space for accommodating components for the operation of the mask apparatus 1 can be defined between the mask body 10 and the mask body cover 20. The sealing bracket 30 and the seal 40 are coupled to the rear surface of the mask body 10 to define the breathing space between the user's face and the mask body 10 and prevent the external air from being introduced into the breathing space.

The mask body 10 can include a cover coupling groove 101. The cover coupling groove 101 can be defined along a front edge of the mask body 10. The cover coupling groove 101 can be defined by a height difference. The cover coupling groove 101 can be defined to correspond to an edge of the mask body cover 20. The cover coupling groove 101 can be defined by recessing a portion of the front surface of the mask body 10 backward. The mask body cover 20 can move toward the cover coupling groove 101 of the mask body 10 to allow the mask body cover 20 to be inserted into the cover coupling groove 101.

The mask body 10 can include a first cover coupling portion 102. An upper portion of the mask body cover 20 can be supported on the first cover coupling portion 102. The first cover coupling portion 102 can be disposed on a front upper portion of the mask body 10.

For example, the first cover coupling portion 102 can have a structure that is capable of being hook-coupled. The hook coupled to the first cover coupling portion 102 can be disposed on a rear surface of the mask body cover 20.

The first cover coupling portion 102 can be provided in plurality, and the hook can also be provided in plurality to correspond to the first cover coupling portions 102. In some examples, the first cover coupling portion 102 can be provided at the left and right sides from the center of the mask body 10, respectively. The first cover coupling portion 102 can be referred to as an upper cover coupling portion.

The mask body 10 can include a first bracket coupling portion 103. The first bracket coupling portion 103 can be disposed above the mask body 10. The first bracket coupling portion 103 can support an upper portion of the sealing bracket 30.

The first bracket coupling portion 103 can be disposed above a rear surface of the mask body 10.

For example, the first bracket coupling portion 103 can be provided by allowing a portion constituting the mask body 10 to protrude forward from the rear surface of the mask body 10. Thus, the first bracket coupling portion 103 can be understood as a recess when viewed from a rear side of the mask body 10 and a protrusion when viewed from a front side of the mask body 10.

The sealing bracket 30 can include a first body coupling portion 304 that has the same shape as the recessed shape of the first bracket coupling portion 103 and is seated on the first bracket coupling portion 103.

The first bracket coupling portion 103 can be provided at each of the left and right sides of the mask body 10. The first bracket coupling portion 103 can be defined as an upper bracket coupling portion.

The mask body 10 can include a support rib 104.

The support rib 104 can be provided to protrude forward from the front surface of the mask body 10. The support rib 104 can contact the rear surface of the mask body cover 20 when the mask body cover 20 is coupled to the mask body 10.

The mask body 10 and the mask body cover 20 can resist external forces acting in a front and rear direction by the support rib 104. The support ribs 104 can be provided in plurality on the front surface of the mask body 10.

The support rib 104 can perform a function of fixing a portion of the control module 18 mounted on the mask body 10. For this, the support rib 104 can include a hook shape. In other words, a hook protrusion can protrude from an end of the support rib 104 to fix the end of the control module 18.

The mask body 10 can include a second cover coupling portion 106.

A lower portion of the mask body cover 20 can be supported on the second cover coupling portion 106. The second cover coupling portion 106 can protrude in a hook shape from a front lower end of the mask body 10. The first cover coupling portion 106 can be provided at each of the left and right sides from the center of the mask body 10. The second cover coupling portion 106 can be defined as a lower cover coupling portion.

A hook catching portion to which the second cover coupling portion 106 is coupled can be disposed on the mask body cover 20, and the hook catching portion can be disposed at each of left and right sides of the mask body cover 20.

The mask body 10 can include a second bracket coupling portion 107.

A lower portion of the sealing bracket 30 can be supported on the second bracket coupling portion 107. The second bracket coupling portion 107 can be provided by opening the mask body 10. The second bracket coupling portion 107 can be disposed in a lower portion of the mask body 10. For example, the second bracket coupling portion 107 can be provided as a through-hole defined in the mask body 10.

A second body coupling portion 305 coupled to the second bracket coupling portion 107 can be disposed on the sealing bracket 30. The second bracket coupling portion 107 can be provided in plurality, and the second body coupling portion 305 can also be provided in plurality to correspond to the second bracket coupling portions 107. In some examples, the second bracket coupling portion 107 can be provided at each of the left and right sides with respect to the center of the mask body 10. The second bracket coupling portion 107 can be defined as a lower bracket coupling portion.

The mask body 10 can include the sensor mounting portion 109.

The sensor mounting portion 109 can have a rib shape in which a portion of the front surface of the mask body 10 protrudes forward. In detail, the sensor mounting portion 109 has a rib shape that is surrounded along an edge of the sensor, and an installation space in which the sensor is installed is defined in the sensor mounting portion 109.

A hole through which the installation space and the breathing space communicate with each other is defined in the mask body 10 corresponding to the inside of the sensor mounting portion 109. The sensor disposed in the installation space can include a pressure sensor, and the pressure sensor can sense pressure information of the breathing space through the hole.

The mask body 10 can include a fan module mounting portion 110.

The fan module mounting portion 110 can include a first fan module mounting portion on which a first fan module 16 is mounted and a second fan module mounting portion on which a second fan module 17 is mounted.

The first fan module mounting portion and the second fan module mounting portion can be disposed on the front surface of the mask body 10. In detail, the first fan module mounting portion can be disposed at the right side of the mask body 10, and the second fan module mounting portion can be disposed at the left side of the mask body 10.

The first fan module 16 and the second fan module 17 can be detachably coupled to the first fan module mounting portion and the second fan module mounting portion, respectively.

The mask body 10 can include an air duct 120.

The air duct 120 can be disposed on the front surface of the mask body 10. A passage through which air passes can be provided in the air duct 120.

The air duct 120 can include a first air duct 120a connected to the first fan module mounting portion and a second air duct 120b connected to the second fan module mounting portion.

The first air duct and the second air duct can be disposed on an edge of the first fan module mounting portion and an edge of the second fan module mounting portion, which are adjacent to the center of the front surface of the mask body 10 so as to be disposed between the first fan module mounting portion and the second fan module mounting portion.

In some implementations, the first fan module mounting portion and the second fan module mounting portion can have a shape symmetrical with respect to a vertical plane (or a vertical line) passing through the center of the front surface of the mask body 10. Similarly, the first air duct and the second air duct can also have a shape symmetrical with respect to the vertical plane or the vertical line passing through the center of the front surface of the mask body 10.

One end of the air duct 120 communicates with the outlets of the fan modules 16 and 17 to allow the external air to be introduced into the air duct 120. In addition, the other end of the air duct 120 communicates with the air outlet 129 so that the air introduced into the air duct 120 is discharged into the breathing space S.

A control module 18 can be mounted on the front surface of the air duct 120.

A control module mounting portion 128 for mounting the control module 18 can be disposed on the front surface of the air duct 120. A portion of the front surface of the air duct 120 can be provided as a flat portion on which the control module 18 is capable of being seated, and the flat portion can be defined as the control module mounting portion 128.

The control module mounting portion 128 can include a first control module mounting portion 128a provided in the first air duct and a second control module mounting portion 128b provided in the second air duct. One control module 18 can be fixed to the first control module mounting portion 128a and the second control module mounting portion 128b, or a plurality of control modules can be respectively fixed to the first and second control module mounting portions 128a and 128b.

The mask body 10 can include a power module mounting portion 130 for mounting the power module 19.

The power module mounting portion 130 can be disposed on the front surface of the mask body 10. The power module mounting portion 130 can be provided at one of the left and the right side of the mask body 10.

The power module mounting portion 130 can be disposed at the side of the fan module mounting portion 110. Specifically, the power module mounting portion 130 can be provided between the fan module mounting portion 110 and a side end of the mask body 10. The side end of the mask body 10 can be defined as an end adjacent to the user's ear when worn. In some implementations, the connector hole 135 can be formed in the side end of the mask body 10, which is provided with the power module mounting portion 130.

The mask body 10 can include a battery mounting portion 140 for mounting a battery.

The battery mounting portion 140 can be disposed on the front surface of the mask body 10. The battery mounting portion 140 can be provided to protrude forward from the front surface of the mask body 10 so as to surround the battery.

For example, the battery mounting portion 140 can include a pair of guide ribs protruding forward from the front surface of the mask body 10 and a connection rib connecting front ends of the pair of guide ribs to each other. In some implementations, the battery can be mounted in a battery accommodation space defined by the pair of guide ribs and the connection rib.

The battery can move downward from an upper side of the battery accommodating space and be inserted into the battery accommodating space and then can move in a reverse direction to be separated. A lower portion of the battery inserted into the battery mounting portion 140 can be supported by an air discharge portion 150 to be described later.

The mask body 10 can include the air discharge portion 150.

The air discharge portion 150 can be disposed in a lower portion of the mask body 10. The air discharge portion 150 can define a flow space through which the air flowing from the first air exhaust hole 154 toward the second air exhaust hole 155 passes.

The air discharge portion 150 can protrude forward from the front surface of the mask body 10. In some implementations, the air discharge portion 150 can extend to be rounded in an arch shape or can extend to be bent several times.

When the mask body cover 20 is coupled to the mask body 10, a front end of the air discharge portion 150 can be in contact with the rear surface of the mask body cover 20, and the inner space of the mask body 10 and the flow space can be partitioned from each other.

The air discharge portion 150 can define a top surface and both side surfaces of the flow space, and a rear surface of the mask body cover 20 can define a front surface of the flow space. In some implementations, the front surface of the mask body 10 can define a rear surface of the flow space, and the bottom surface of the mask body 10 on which the second air exhaust hole 155 is defined can define a bottom surface of the flow space.

The top surface of the air discharge portion 150 can support a lower end of the battery. Both lower ends of the air discharge portion 150 having the arch shape or tunnel shape can be connected to the bottom surface of the mask body 10, and the bottom surface of the mask body 10 can be defined by the rib extending forward from the lower end of the front surface of the mask body 10. The cover coupling groove 101 is recessed along the front end of the rib defining the bottom surface of the mask body 10, and the lower end of the rear surface of the mask body cover 20 is coupled to the cover coupling groove 101.

The first air exhaust hole 154 can be defined in the front surface of the mask body 10 defining the rear surface of the flow space.

The mask body cover 20 can include a pair of filter mounting portions 21 and 22, as described above.

The filter mounting portions 21 and 22 can be provided by recessing the front surface of the mask body cover 20 recessed by a predetermined depth toward the rear surface of the mask body cover 20. Filters 23 and 24 are accommodated inside the filter mounting portions 21 and 22, and filter covers 25 and 26 can be mounted on edges of the filter mounting portions 21 and 22 in the state in which the filters 23 and 24 are accommodated.

An air suction hole 211 can be defined in each of the filter mounting portions 21 and 22. The air suction hole 211 can communicate with suction holes defined in the front surfaces of the fan modules 16 and 17. An edge of the air suction hole 211 can have an inclined surface that inclined in a direction in which a diameter gradually decreases from the front surface to the rear surface.

A filter cover mounting groove 212 for fixing each of the filter covers 25 and 26 can be defined in a side surface of each of the filter mounting portions 21 and 22. A coupling protrusion inserted into the filter cover mounting groove 212 and 222 can be disposed on each of the filter covers 25 and 26. In FIG. 5, only the coupling protrusion 262 disposed on the left filter cover 26 is illustrated, but the same coupling protrusion can be disposed on the right filter cover 25 as well. A sealing material for sealing can be provided between the edge of the rear surface of the air suction hole 211 of the filter mounting portions 21 and 22 and the fan inlets of the fan modules 16 and 17. The sealing material can surround the air suction hole 211 and edges of the fan inlets of the fan modules 16 and 17 to prevent the external air from being introduced.

The filter mounting portions 21 and 22 include a first filter mounting portion 21 provided at the right side of the mask body cover 20 and a second filter mounting portion 22 provided at the left side of the mask body cover 20.

The air suction hole defined in the first filter mounting portion 21 can be defined as a first air suction hole 211, and the air suction hole defined in the second filter mounting portion 22 can be defined as a second air suction hole.

The filters 23 and 24 can include a first filter 23 accommodated inside the first filter mounting portion 21 and a second filter 24 accommodated inside the second filter mounting portion 22.

The filter covers 25 and 26 can include a first filter cover 25 mounted on the first filter mounting portion 21 and a second filter cover 26 mounted on the second filter mounting portion 22. A plurality of first air inlets 251 can be defined in the first filter cover 25 to allow the external air to be introduced, and a plurality of second air inlets 261 can be defined in the second filter cover 26 to allow the external air to be introduced.

The control module 18 can be referred to as a first electronic circuit component, and the power module 19 can be referred to as a second electronic circuit component.

The fan modules 16 and 17 can include a fan, a fan motor, and a fan housing accommodating the fan and the fan motor. The fan housing can include a suction hole through which the external air is introduced into the fan, and a discharge hole through which the air forcedly flowing by the fan is discharged.

The fan can include various types of fans. For example, the fan can include a centrifugal fan that suctions air from the front side of the mask body cover 20 and discharges the air to the side of the mask body 10. In some cases, the fan can include an axial fan or a cross flow fan.

The air introduced through the first air inlet 251 to pass through the first filter 23 is suctioned through the first air suction hole 211. In some implementations, the air introduced through the second air inlet 261 to pass through the second filter 24 is suctioned through the second air suction hole 221.

The fan outlet of the first fan module 16 can communicate with the first air duct to discharge the air to the breathing space, and the fan outlet of the second fan module 17 can communicate with the second air duct to discharge the air to the breathing space.

The control module 18 can control an operation of the mask apparatus 1. The control module 18 can be fixed to the control module mounting portion 128.

The control module 18 can include a communication module to transmit and receive various types of information. The control module 18 can include a data storage module to store various types of information.

The control module 18 can control an operation of each of the fan modules 16 and 17. In detail, the control module 18 can control the operation of each of the fan modules 16 and 17 based on information sensed from the sensor.

The control module 18 can be electrically connected to the power module 19, the fan modules 16 and 17, and the battery so as to be interlocked with each other.

The power module 19 can receive power from the outside. The power module 19 can include a charging circuit for charging the battery. The power module 19 can include the connector 192 and the manipulation portion 195. Thus, the control module 18 can be operated by receiving battery power or external power through the connector 192.

The power module 19 can control supply of power to the mask apparatus 1 by the manipulation portion 195. In detail, the power module 19 can control supply of power from the battery to the control module 18 and the fan modules 16 and 17.

The seal 40 can be coupled to the rear surface of the mask body 10 by the sealing bracket 30 to be in close contact with the user's face.

The rear surface of the mask body 10 can be to be spaced apart from the user's face by the seal 40.

The sealing bracket 30 can be provided in a ring shape forming a closed loop. The seal 40 can be detachably coupled to the filter bracket 30.

In some implementations, the sealing bracket 30 is coupled to be detachable from the mask body 10 to separate the sealing bracket 30 from the mask body 10. With this structure, only the sealing bracket 30 can be separated, or an assembly of the seal 40 and the sealing bracket 30 can be separated from the mask body 10 to clean only sealing bracket 30 or clean both the sealing bracket 30 and the seal 40.

After the seal 40 is coupled to the sealing bracket 30, the sealing bracket 30 is coupled to the mask body 10, then the seal 40 is stably fixed to the mask body 10.

The sealing bracket 30 can include a sealing insertion portion 301 inserted into an inner edge of the seal 40.

The inner edge of the seal 40 can be provided in a shape of seal lips that is branched into two portions, and the sealing insertion portion 301 can be inserted into the seal lips.

The sealing insertion portion 301 can have a cross-sectional shape having a constant thickness or a cross-sectional shape of which a thickness decreases from an inner edge toward an outer edge. A body of the sealing bracket 30 can be provided by the sealing insertion portion 301 and a fixing guide 302 to be described later.

The sealing bracket 30 can include the fixing guide 302.

The fixing guide 302 can be bent at an inner end of the sealing insertion portion 301. When the sealing insertion portion 301 is completely inserted into the seal lips of the seal 40, one of the two seal lips is in contact with the fixing guide 302. That is, when the inner edge of the seal 40 is in contact with the fixing guide 302, it can be understood that the seal 40 is completely coupled to the sealing bracket 30.

The sealing bracket 30 can include a bracket insertion portion 306 coupled to the mask body 10. The bracket insertion portion 306 is inserted into a cutoff portion defined in the rear surface of the mask body 10 to cover a portion of an edge of the cutoff portion.

The cutoff portion can be understood as an opening communicating with the air duct 120 so that the air passes therethrough. The bracket insertion portion 306 can be disposed on one edge of the cutoff portion, specifically, an outer edge.

The air outlet 129 already described can be understood as the remaining portion of the cutoff portion that is not covered by the bracket insertion portion 306 in a state in which the bracket insertion portion 306 is inserted into one side of the cutoff portion.

When the bracket insertion portion 306 is inserted into or coupled to the one side of the cutoff portion to shield the one side of the cutoff portion, the air discharged from the fan modules 16 and 17 can pass between the air duct 120 and the bracket insertion portion 306 to flow to the air outlet 129.

The bracket insertion portion 306 can perform a function of fixing the sealing bracket 30 to the mask body 10 while defining one surface of the air duct 120. In detail, an upper portion of the sealing bracket 30 can be fixed to the upper portion of the mask body 10 by the first body coupling portion 304, a lower portion of the sealing bracket 30 can be fixed to the lower portion of the mask body 10 by the second body coupling portion 305, and an intermediate portion of the sealing bracket 30 can be fixed to an intermediate portion of the mask body 10 by the bracket insertion portion 306.

The seal 40 can be made of a material having elasticity. The seal 40 can be in close contact with the user's face and deformed to correspond to a facial contour of the user. The seal 40 can be provided in a ring shape forming a closed loop. The seal 40 can be provided to cover the user's nose and mouth.

The seal 40 includes a coupling portion 400a coupled to the mask body 10, a side surface portion 400c extending from the coupling portion 400a toward the user's face, and a contact portion 400b that is bent from an end of the side surface portion 400c to extend toward the coupling portion 400a.

The contact portion 400b can be a portion that is in close contact with the user's face, and the side surface portion 400c and the contact portion 400b can be angled at an angle of about 90 degrees or less to define a space between the side surface portion 400c and the contact portion 400b.

A first opening can be defined inside the coupling portion 400a of the seal 40, and a second opening can be defined inside the contact portion 400b. As illustrated in FIG. 3, the second opening can include a main opening in which the front of the user's nose and mouth are disposed and a sub opening extending from an upper end of the main opening and disposed on the user's nose.

In some implementations, a lower portion of the main opening, that is, a portion that is in close contact with the front of the user's jaw can be designed closer to the mask body 10 than a portion that is in close contact with the front of the user's cheek.

In some implementations, a plurality of ventilation holes can be defined in the contact portion 400b to minimize a phenomenon in which moisture is generated on the user's cheek. The plurality of ventilation holes can have different sizes, and as an example, a diameter of the ventilation hole can gradually increase from an inner edge to an outer edge of the contact portion 400b.

The air outlet 129 and the air exhaust holes 154 and 155 can be provided inside the first opening, and the user's nose and mouth can be disposed inside the second opening.

The seal 40 is disposed between the user's face and the mask body 10, and the breathing space S is defined by the coupling portion 400a, the contact portion 400b, and the inner side of the side surface portion 400c of the seal 40.

A bracket insertion groove 401 can be defined in an end of the coupling portion 400a of the seal 40.

The bracket insertion groove 401 can be understood as a groove or a space defined between the two seal lips when the coupling portion 400a has the shape that is branched into the two seal lips as described above, and the bracket insertion portion 306 of the sealing bracket 30 is inserted into the bracket insertion groove 401.

The seal 40 includes a first seating portion 404 on which the first body coupling portion 304 is seated, a second seating portion 405 on which the second body coupling portion 305 is seated, and a third seating portion 406 on which the bracket insertion portion 306 is seated.

The first and third seating portions 404 and 406 can be understood as grooves in which a portion of the seal 40 is cut to form an accommodation space in which the first body coupling portion 304 and the bracket insertion portion 306 are accommodated. In some implementations, the second seating portion 405 can be understood as a hole in which a portion of the seal 40 is cut to pass through the second body coupling portion 305.

In another aspect, the first seating portion 404 can be defined as a first opening, the second seating portion 405 can be defined as a second opening, and the third seating portion 406 can be defined as a third opening.

Figure 6:
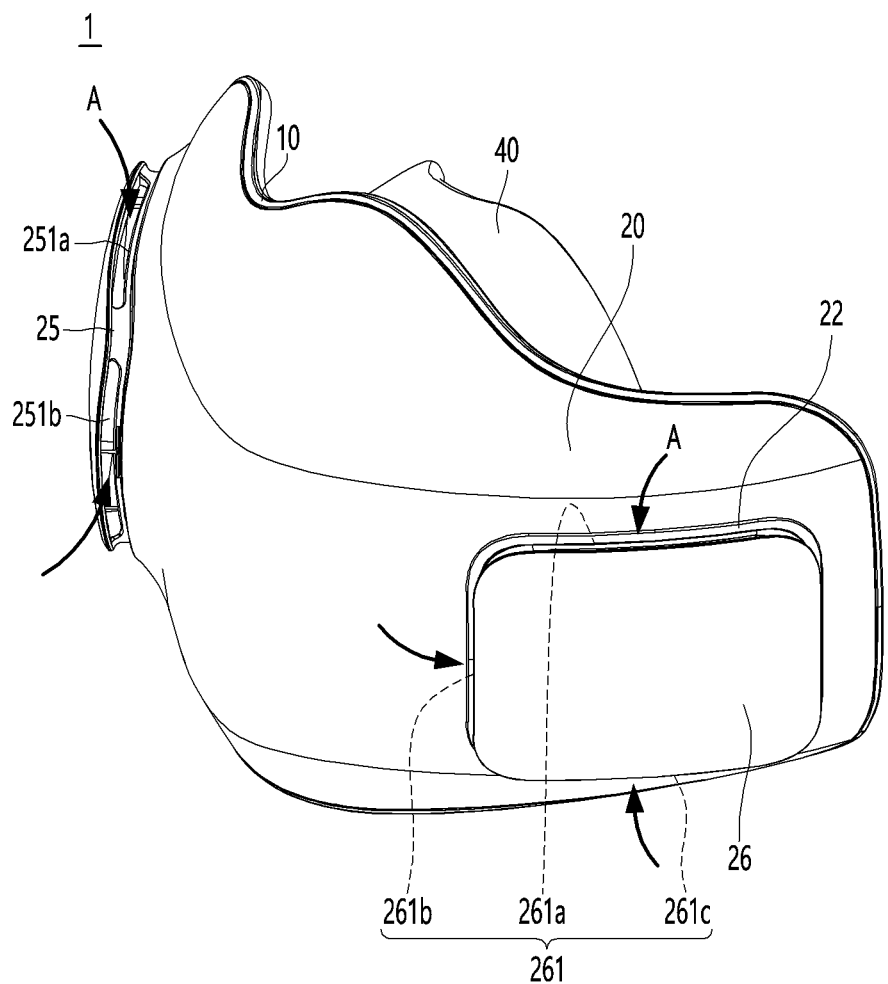
FIGS. 6 and 7 are views illustrating examples of flow of air when the mask apparatus is operated.
Figure 7:
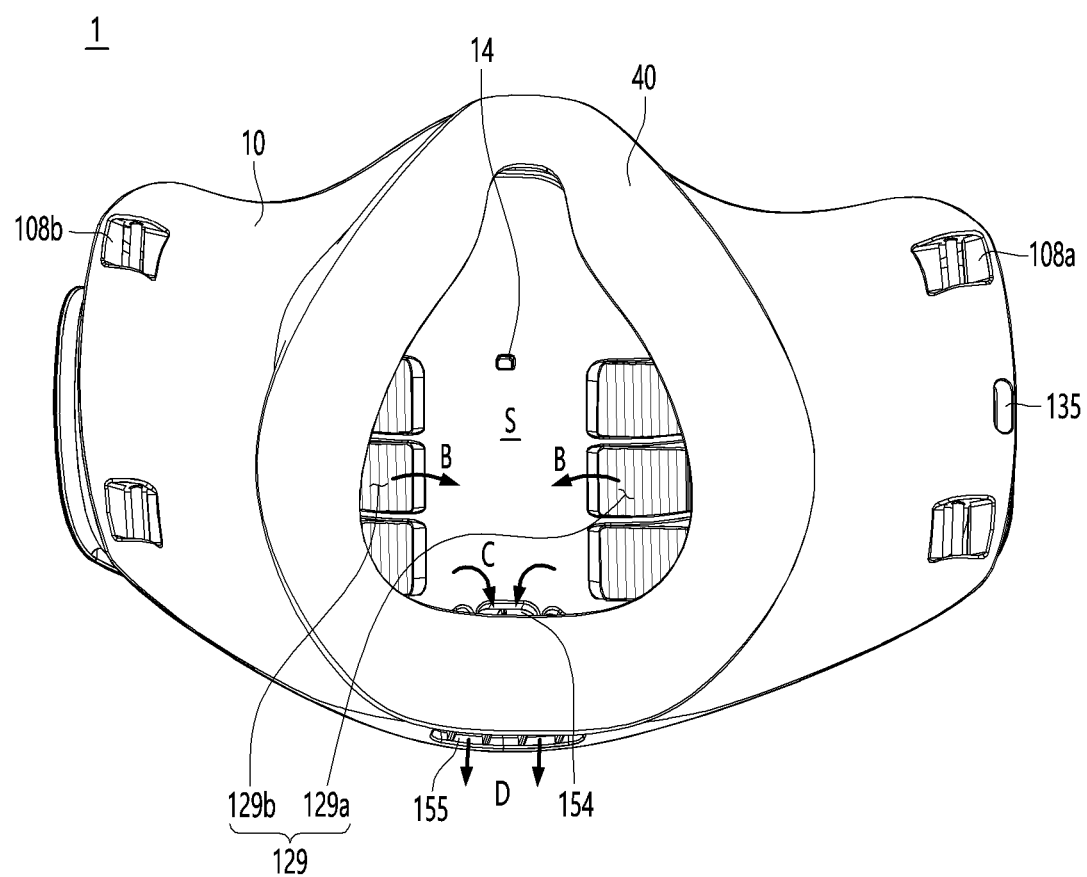

FIGS. 6 and 7 are views illustrating examples of flow of air when the mask apparatus is operated.

Referring to FIGS. 6 and 7, the mask apparatus 1 can suction the external air through the air inlets 251 and 261 provided in the filter covers 25 and 26. The flow direction of the external air suctioned into the mask apparatus 1 is indicated by an arrow "A." Since the air inlets 251 and 261 are provided in plurality to suction the air in various directions, an inflow rate of the external air increases.

For example, the air inlets 251 and 261 can include air inlets 251a and 261a configured to suction air flowing at upper sides of the filter covers 25 and 26, air inlets 251b and 261b configured to suction air flowing at a front side of the filter covers 25 and 26, and air inlets 251c and 261c configured to suction air flowing at a lower side of the filter covers 25 and 26. The side air inlets 251b and 261b can be provided at one or both sides of the left and right sides of the filter covers 25 and 26.

Since the filter covers 25 and 26 in which the air inlets 251 and 261 are provided are respectively disposed at left and right sides of the front surface of the mask apparatus 1, the external air can be smoothly suctioned from the left and right sides of the front surface of the mask apparatus 1.

The external air introduced through the air inlets 251 and 261 can be filtered by passing through the filters 23 and 24 disposed inside the filter mounting portions 21 and 22. The filters 23 and 24 can be replaced when the filter covers 25 and 26 are separated from the mask apparatus 1.

The air passing through the filters 23 and 24 can be introduced into the suction holes of the fan modules 16 and 17 through the air suction hole 211. Since the filter mounting portions 21 and 22 in which the air suction hole 211 is defined and the fan modules 16 and 17 are assembled in the state of being in close contact with each other, the air passing through the filter can be prevented from leaking, or the external air can be prevented from being introduced between the filter mounting portions 21 and 22 and the fan modules 16 and 17.

The air discharged through the fan outlets of the fan modules 16 and 17 can pass through the air duct 120 to flow into the breathing space S through the air outlet 129. A flow direction of the air introduced into the breathing space S through the air outlet 129 is indicated by an arrow "B."

The breathing space S can be defined by the mask body 10 and the seal 40. When the mask body 10 is in close contact with the user's face, the seal 40 can be in close contact with the mask body 10 and the user's face to form an independent breathing space that is separated from the external space.

The air that the user exhales after suctioning the filtered air supplied through the air outlet 129 can be exhausted to the external space through the air exhaust holes 154 and 155.

As described above, the air exhaust holes 154 and 155 include a first air exhaust hole 154 communicating with the breathing space and a second air exhaust hole 155 communicating with the external space, and the first air exhaust hole 154 and the second air exhaust hole 155 can communicate with each other by the flow space defined by the air discharge portion 150. The air exhaled by the user can be guided into the flow space through the first air exhaust hole 154. A flow direction of the air flowing into the flow space through the first air exhaust hole 154 is indicated by an arrow "C."

The air guided into the flow space through the first air exhaust hole 154 can be discharged to the external space through the second air exhaust hole 155. A flow direction of the air flowing to the external space through the second air exhaust hole 155 is indicated by an arrow "D."

Figure 8:
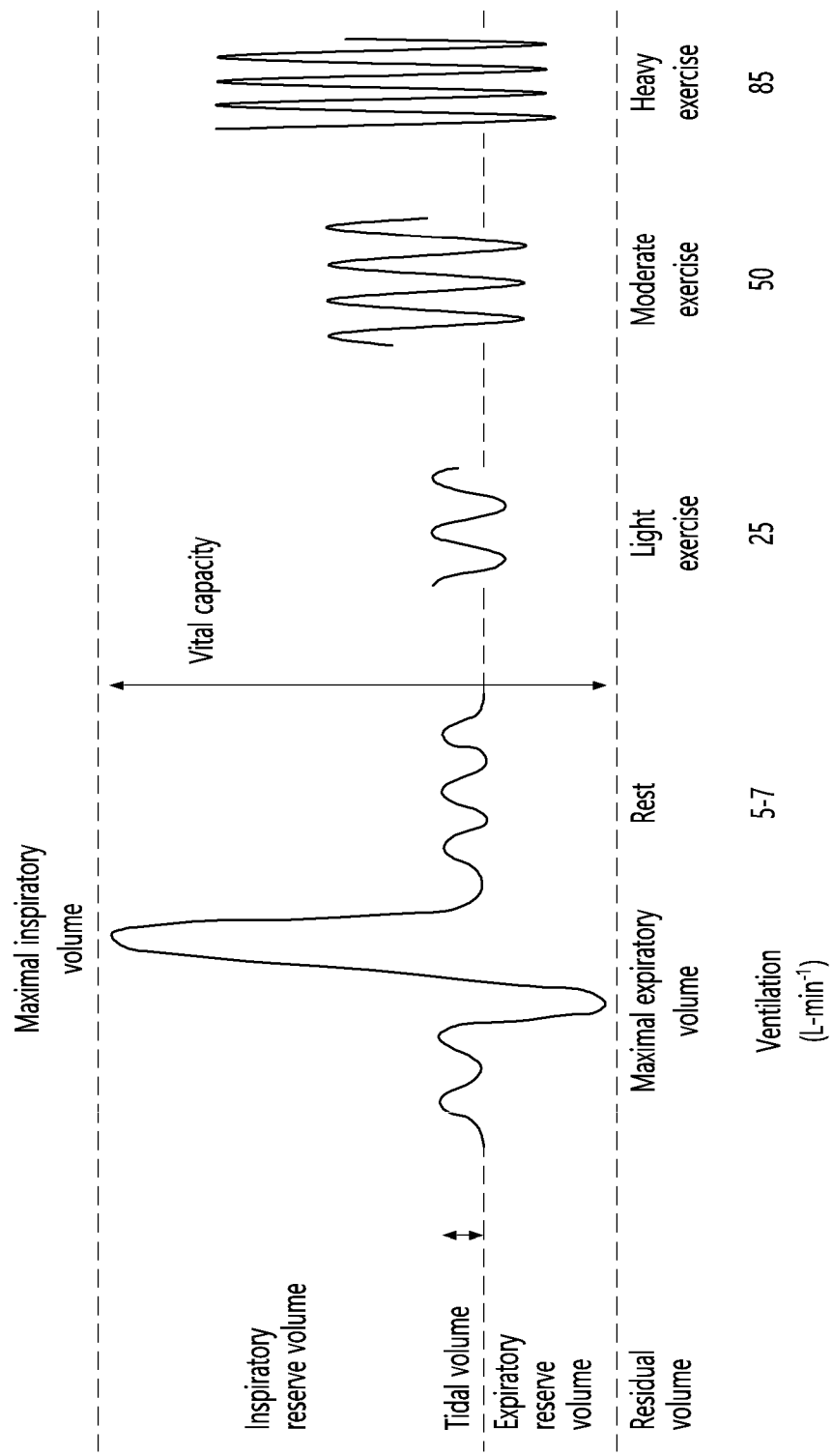
FIG. 8 is a graph illustrating an example of a change in air volume in lungs according to an amount of exercise of a person.

FIG. 8 is a graph illustrating an example of a change in air volume in lungs according to an amount of exercise of a person.

In FIG. 8, a horizontal axis of the graph indicates elapse of time, and a vertical axis of the graph indicates an amount (a pressure value) of air remaining in the lungs.

Referring to FIG. 8, when a person inhales or exhales, a certain amount of air can enter the lungs. The amount of air inhaling once (tidal air) generally in a normal state or ordinary state can vary from person to person. For example, in a stable state, that is, in a state of rest, a user can have a ventilation of approximately 5 L to about 7 L for about one minute. Here, the ventilation can be understood as a cumulative amount of air inhaling during the breathing for one minute.

However, when the person moves or exercises, a greater amount of air can enter the lungs than the amount of air at the stable state. For example, if the user do light exercise, the user can have a ventilation that is equivalent to approximately 25 L for one minute, and if you do heavy exercise, user can have a ventilation that is equivalent to approximately 85 L for about one minute.

That is, it can be seen that more ventilation (air volume) is needed in the state of exercising than in the state of rest.

In some implementations, when the person is moving or exercising, the breathing cycle can be faster than in the stable state. For example, the person's cycle of inhalation and exhalation can be faster in the exercising state rather than the rest state.

In some implementations, the mask apparatus (e.g., controller) can determine the user's breathing state by detecting the internal pressure (air volume) of the mask when the user wears the mask apparatus, thereby can accurately determine whether the user is in the rest state or whether the user is on an exercise. In some implementations, appropriate external air can be provided in consideration of the determined current state of the user.

Figure 9:
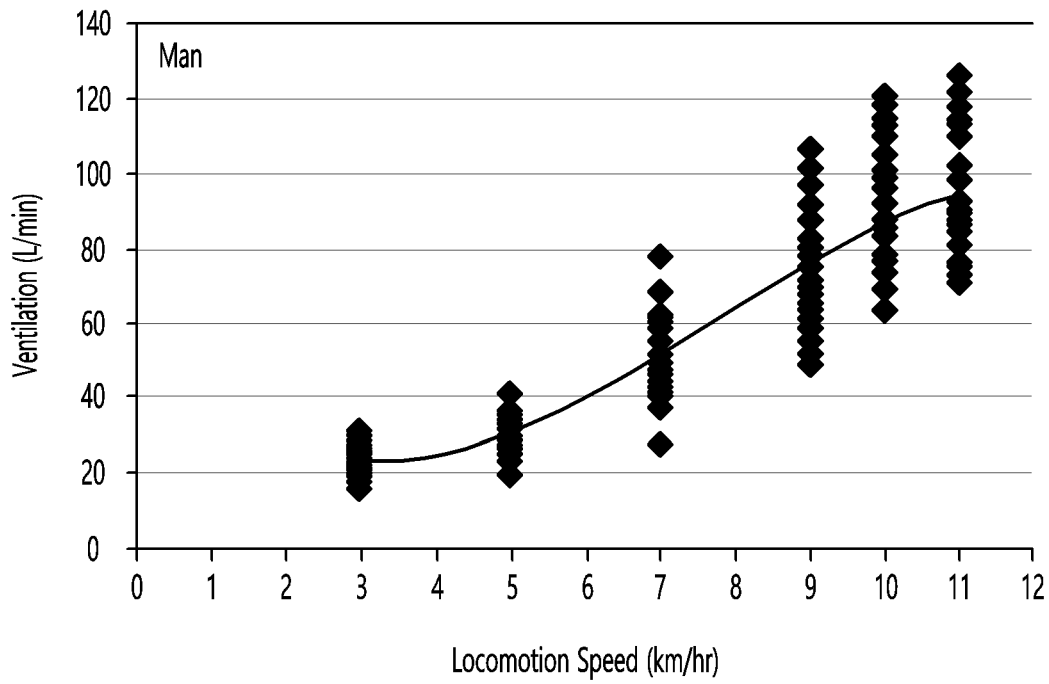
FIG. 9 is a graph illustrating an example of a change in ventilation of a male according to exercise intensity.
Figure 10:
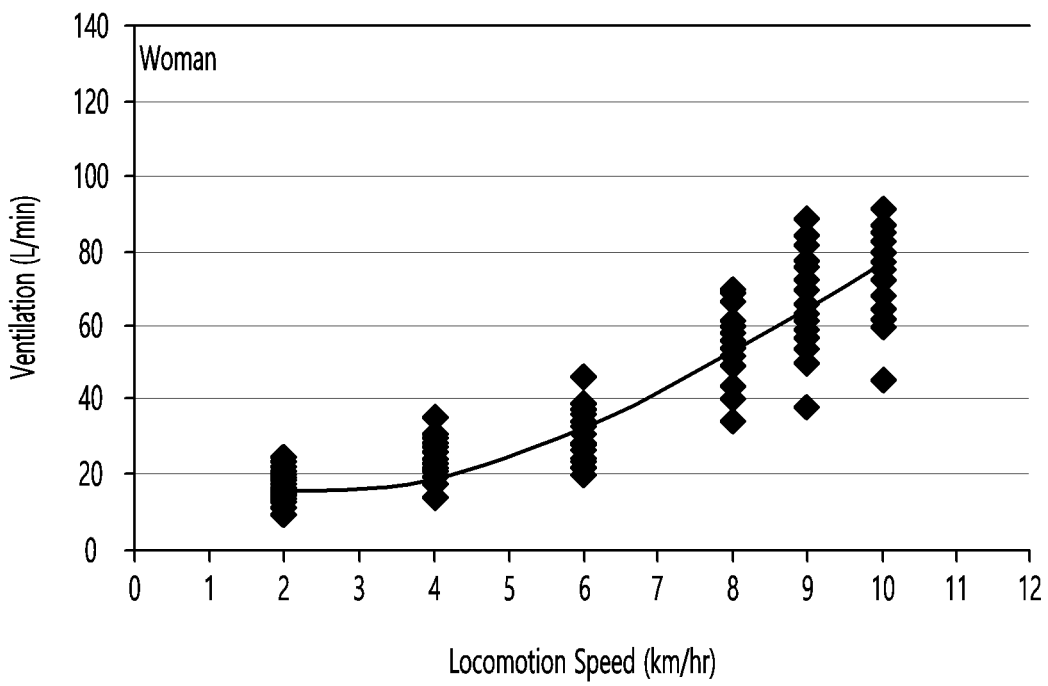
FIG. 10 is a graph illustrating an example of a change in ventilation of a female according to exercise intensity.

FIG. 9 is a graph illustrating an example of a change in ventilation of a male according to exercise intensity, and FIG. 10 is a graph illustrating an example of a change in ventilation of a female according to exercise intensity.

In FIGS. 9 and 10, a horizontal axis of the graph indicates an intensity of exercise, and a vertical axis of the graph indicates a required ventilation. This graph illustrates the trend of the required ventilation for each experimental group at exercise intensities of approximately 3 km/hr, approximately 5 km/hr, approximately 7 km/hr, approximately 9 km/hr, approximately 10 km/hr, and approximately 11 km/hr.

Referring to FIGS. 9 and 10, it is seen that in general, when male and female exercise at a heavy exercise intensity compared to exercise at a light exercise intensity, the ventilation significantly increases.

In some implementations, it is seen that when the user exercises at a heavier exercise intensity than at a light exercise intensity, there is a greater variation in ventilation for each individual.

That is, when the user wears the mask in the stable state, if a certain amount of air is supplied into the mask, there can be no great inconvenience in breathing. However, in the case of high-activity exercise, there is a large variation in ventilation for each individual, and thus it is necessary to provide an amount of air, which is suitable for the user's characteristics.

Figure 11:
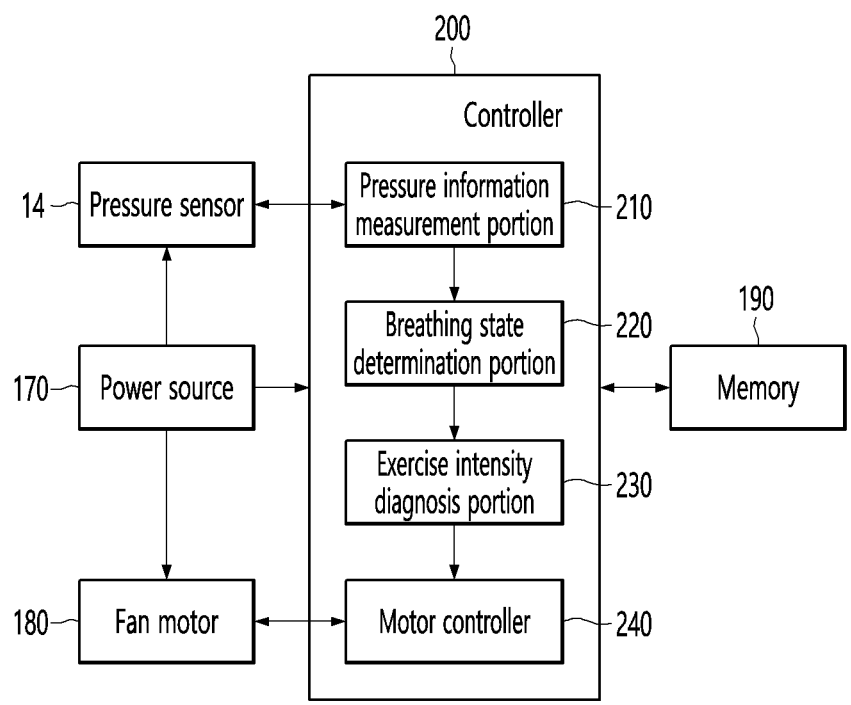
FIG. 11 is a block diagram illustrating example components of the mask apparatus.

FIG. 11 is a block diagram illustrating example components of the mask apparatus.

Referring to FIG. 11, the mask apparatus 1 includes at least some or all of a pressure sensor 14 (see FIG. 7), a power source 170, a fan motor 180, a memory 190, and a controller 200.

The pressure sensor 14 is mounted on a sensor mounting portion 109 to sense an internal pressure of the mask apparatus 1.

Here, the internal pressure of the mask apparatus 1 can mean a pressure of a breathing space S defined by a user's face and a seal 40.

The pressure sensor 14 can be an air pressure sensor that measures a pressure or air pressure in a sealed space by using a flow rate or wind strength of air flowing into the mask apparatus 1. Alternatively, the pressure sensor 14 can be a differential pressure sensor that measures a pressure change in a sealed space. Since the pressure sensor 14 is the well-known technology, a detailed description thereof will be omitted.

Information measured by the pressure sensor 14 can be transmitted to the controller 200 or can be stored in the memory 190. The memory 190 can be a non-transitory memory. The controller 200 can include an electric circuit, one or more processors, or the like, can control operation of components of the mask apparatus 1 such as the pressure sensor 14 and the fan modules 16 and 17.

The power source 170 functions to provide power to the pressure sensor 14, the fan motor 180, and the controller 200.

The power source 170 can be provided as a battery or a power module 19 mounted on the mask apparatus 1. The power source 170 can be charged in a wire or wireless manner by an external power supply device.

The fan motor 180 provides power to allow a first fan module 16 and a second fan module 17 to rotate. The fan motor 180 can operate at least one of the first fan module 16 and the second fan module 17. The rotation speed of each of the first fan module 16 and the second fan module 17 can vary depending on a rotation speed of the fan motor 180.

The fan motor 180 can be controlled by the controller 200, and the controller 200 (or microcomputer) can be understood as a semiconductor chip or an electronic component provided to the control module 18.

The memory 190 can store the information sensed by the pressure sensor 14. Particularly, the memory 190 can store a pressure value sensed by the pressure sensor 14, an inhalation time, an exhalation time, a tidal volume, a breathing cycle, and a next breathing cycle, which are analyzed through the pressure value. For reference, the inhalation time can be understood as an inhalation duration, and the exhalation time can be understood as an exhalation duration.

Information processed by the controller 200 can be stored in the memory 190. The information processed by the controller 200 can be updated and stored in the memory 190. The memory 190 can be understood as a semiconductor chip or an electronic component provided to the control module.

The controller 200 can analyze the information sensed by the pressure sensor 14 and control the rotation speed (rpm) of the fan motor 180 based on the analyzed information.

Particularly, the controller 200 can include a pressure information measurement portion 210, a breathing state determination portion 220, an exercise intensity diagnosis portion 230, and a motor controller 240.

The pressure information measurement portion 210 controls the pressure sensor 14 to measure the internal pressure of the mask. The pressure information measurement portion 210 can continuously sense the internal pressure of the mask after power of the mask apparatus 1 is turned on. Alternatively, the pressure information measurement portion 210 can sense the internal pressure of the mask from an input point in a specific operation mode.

The pressure values sensed by the pressure sensor 14 can be transmitted to the pressure information measurement portion 210 in real time.

The breathing state determination portion 220 determines a user's breathing state by analyzing the information measured by the pressure information measurement portion 210.

For example, the breathing state determination portion 220 can determine the breathing state by using a maximum pressure value and a minimum pressure value among the pressure values, which are sensed by the pressure sensor 14.

Particularly, the breathing state determination portion 220 can calculate a difference value between the maximum pressure value and the minimum pressure value, which are sensed by the pressure sensor 14, and compare the difference value with a reference value to determine the type of breathing state.

When the difference value is less than the first reference value, the breathing state determination portion 220 can determine that the mask is not worn.

If the difference value is greater than the first reference value and less than a second reference value, the breathing state determination portion 220 can determine that the breathing is in a stable state.

In some implementations, when the difference value is greater than the second reference value, the breathing state determination portion 220 can determine that the breathing is in an exercise state.

For another example, the breathing state determination portion 220 can calculate a time difference between a first time at which the maximum pressure value is sensed and a second time at which the minimum pressure value is sensed, among the pressure values sensed by the pressure sensor 14 and compare the time difference with a reference time to determine the kind of breathing state.

When the time difference is less than the first reference time, the breathing state determination portion 220 can determine that the breathing is in the exercise state.

The breathing state determination portion 220 can determine that the breathing is in the stable state when the time difference is greater than the first reference time and less than the second reference time.

In some implementations, when the time difference is greater than the second reference time, the breathing state determination portion 220 can determine that the breathing is in an abnormal state.

That is, the breathing state determination portion 220 can analyze a specific pressure value and/or a time point corresponding to the specific pressure value and determine whether the user is breathing in a stable manner, is breathing abnormally, is exercising, or is not wearing a mask.

The exercise intensity diagnosis portion 230 can determine the user's exercise intensity (exercise amount) using the information transmitted from the pressure information measurement portion 210 and the breathing state determination portion 220.

When the exercise intensity diagnosis portion 230 determines that the breathing is in the stable state through the breathing state determination portion 220, the fan motor 180 can be controlled with reference to table values stored in the memory 190 in the form of a lookup table.

The table values stored in the memory 190 can include information related to a tidal volume, a breathing cycle, a next breathing cycle, an inhalation time, and an exhalation time. The table values can be set as default values when the mask is initially used. For example, the ventilation (e.g., about 500 ml) that a healthy normal adult inhales once can be applied to the table values.

However, since the ventilation is different according to individual deviations, the table values need to be updated according to individual characteristics. Therefore, when the exercise intensity diagnosis portion 230 determines that the breathing is in the stable state through the breathing state determination portion 220, the calculated tidal volume and the inhalation time can be stored in the memory 190 to update tidal volume information.

The motor controller 240 controls the fan motor 180 to control the rotation speed of each of the first fan module 16 and the second fan module 17. The motor controller 240 can control the rotational speed (rpm) of the fan motor 180 according to the exercise intensity (e.g., stable state, light exercise, heavy exercise, etc.) determined by the exercise intensity diagnosis portion 230.

For example, the motor controller 240 can drive the fan motor 180 at a low speed when in the stable state, drive the fan motor 180 at a medium speed when in the light exercise state, and drive the fan motor 180 at a high speed when in the heavy exercise state.

Figure 12:
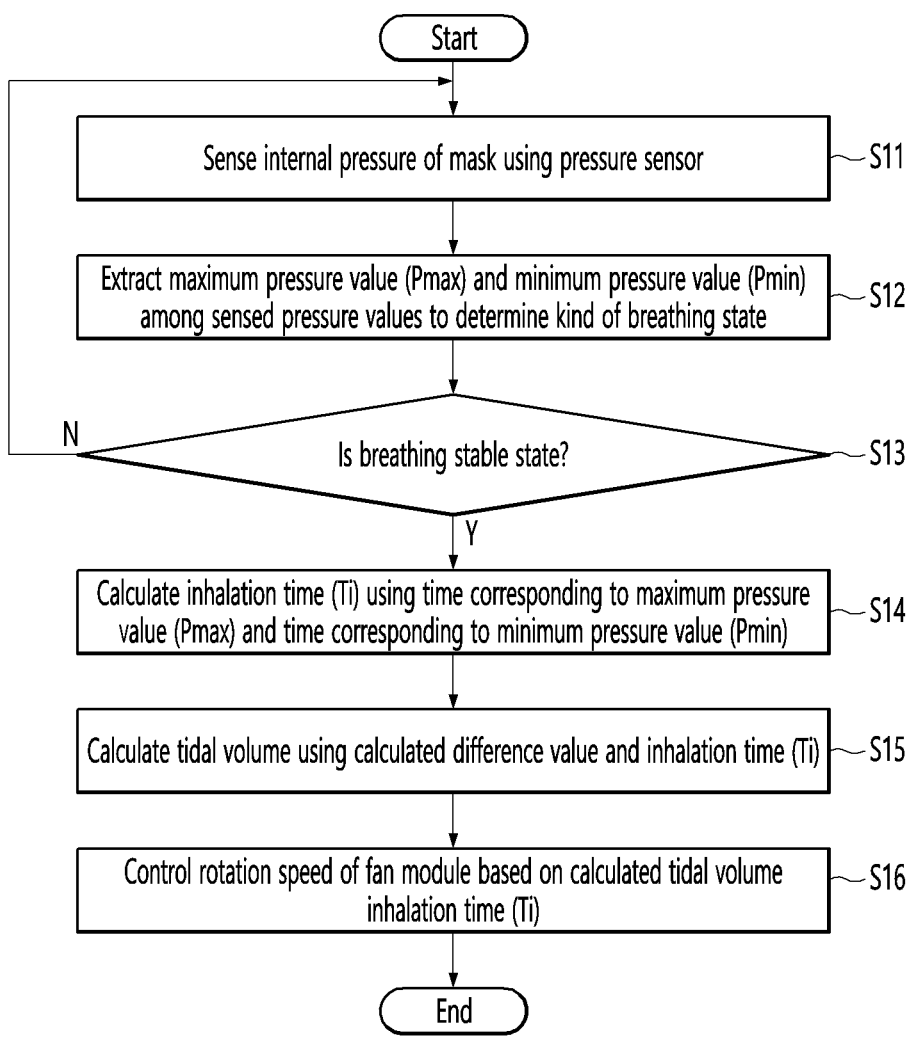
FIG. 12 is a flowchart illustrating an example of a method for controlling a mask apparatus.
Figure 13:
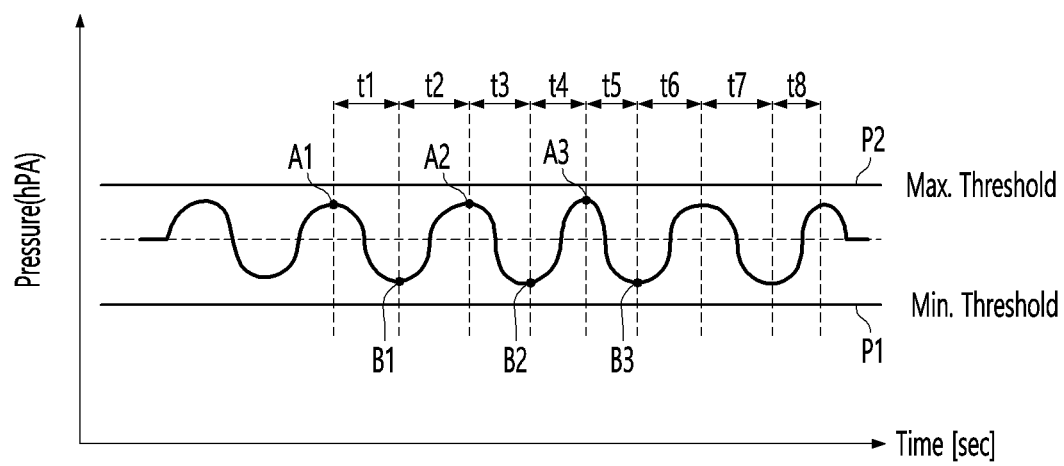
FIG. 13 is a graph illustrating an example of a change in pressure of a breathing space, which is sensed by a pressure sensor.
Figure 14:
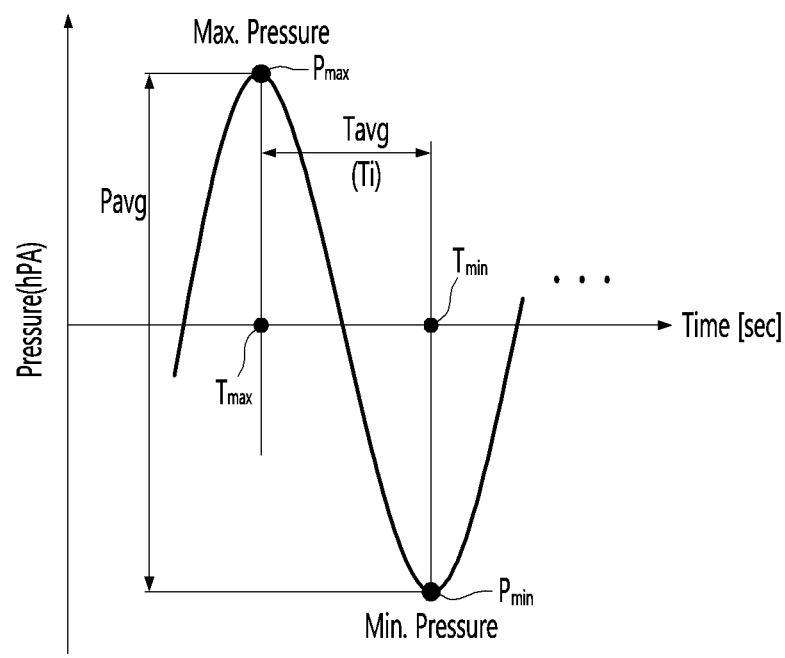
FIG. 14 is a view illustrating an example of a pressure change cycle for a tidal volume.

FIG. 12 is a flowchart illustrating an example of a method for controlling a mask apparatus, FIG. 13 is a graph illustrating an example of a change in pressure of a breathing space, which is sensed by a pressure sensor, and FIG. 14 is a view illustrating an example of a pressure change cycle for a tidal volume.

First, referring to FIG. 12, when the power of the mask apparatus 1 is turned on, the mask apparatus 1 senses an internal pressure of the mask using the pressure sensor 14 (S11).

Here, the internal pressure of the mask can mean a pressure of the breathing space S defined by the user's face and the seal 30 as described above.

In some implementations, when the power is supplied to the mask apparatus 1, the fan modules 16 and 17 can operate, and the fan modules 16 and 17 can rotate at a predetermined rotation speed (RPM), and thus, the breathing can be smoothly performed in the breathing space of the mask apparatus 1. The predetermined rotation speed can be a low speed among the low speed, the medium speed, and the high speed.

The mask apparatus 1 can extract an internal pressure value of the mask for a predetermined time through the pressure sensor 14. In some implementations, the controller 200 can obtain a pressure change graph as illustrated in FIG. 13 based on the pressure value from the pressure value received from the pressure sensor 14.

When the fan modules 16 and 17 operate, the external air can be suctioned into the fan modules 16 and 17 after passing through filter covers 25 and 26 and filters 23 and 24. In addition, the air suctioned into the fan modules 16 and 17 can be introduced into the breathing space S through an air duct 120 and air outlets 129a and 129b. Then, a user can inhale and exhale the air introduced into the breathing space S.

Here, when the user inhales (inspiration) external air into the breathing space S, a pressure in the breathing space S can decrease. On the other hand, when the user exhales air into the breathing space S, a pressure of the breathing space S can increase.

As described above, the pressure in the breathing space S can decrease or increase depending on a user's breathing state (inhalation or exhalation). In some implementations, the pressure or the pressure change in the breathing space can be sensed by the pressure sensor 14. The pressure information or pressure change information sensed by the pressure sensor 14 can be provided to the controller 200 in real time.

The controller of the mask apparatus 1 extracts a maximum pressure value (Pmax) and a minimum pressure value (Pmin) from the pressure values sensed and transmitted by the pressure sensor 14 and then processes the data to determine kinds of breathing state (S12). Then, the controller of the mask apparatus 1 determines whether the determined breathing state is the stable state (S13).

Particularly, the mask apparatus 1 can determine the breathing state of the mask user using the pressure data sensed through the pressure sensor 14.

For example, as illustrated in FIGS. 13 and 14, the mask apparatus 1 collects the pressure data sensed by the pressure sensor 14 for a predetermined time. The pressure data can include pressure values measured in real time. Thus, a time (one time breathing cycle) taken for one time breathing (one time inhalation and one time exhalation) and a maximum pressure value Pmax and a minimum pressure value Pmin for the one time breathing cycle can be calculated, and the next breathing cycle can be predicted.

As described above, when the user inhales air (inhalation), the air in the breathing space can be introduced into the user's respiratory so that the pressure in the breathing space gradually decreases, and when the user exhales air (exhalation), the air can be introduced from the respiratory into the breathing space so that the pressure of the breathing space gradually increases.

As a result, points A1, A2, and A3 at which the pressure of the breathing space is the highest are points at which the exhalation is finished, and points B1, B2, and B3 at which the pressure of the breathing space is the lowest are points at which the inhalation is finished. Therefore, the inhalation starts for a predetermined time from the points A1, A2, and A3 at which the exhalation is finished, and the exhalation starts for a predetermined time from the points B1, B2, and B3 at which the inhalation is finished. According to this principle, the mask apparatus 1 can expect the user's breathing cycle, i.e., the expected inhalation time points A1, A2, and A3 and the expected exhalation time points B1, B2, and B3.

In some implementations, the mask apparatus 1 can compare a difference value Pavg between the maximum pressure value Pmax and the minimum pressure value Pmin, which are sensed by the pressure sensor 14, with a reference value to determine the type of breathing state.

For example, when the difference value Pavg is greater than the first reference value P1 and less than the second reference value (P2>P1), it can be determined that the breathing is in the stable state.

Here, the first reference value P1 can be defined as a minimum threshold value for determining whether the breathing is in the stable state, and the second reference value P2 can be defined as a maximum threshold value for determining whether the breathing is in the stable state. That is, in general, in the stable breathing state, the difference value Pavg can be greater than the first reference value P1 and less than the second reference value P2.

Here, it is reiterated that the maximum pressure value and the maximum threshold value and the minimum pressure value and the minimum threshold value should not be confused. That is, the difference value Pavg between the maximum pressure value and the minimum pressure value can vary according to the breathing state, and the difference value Pavg can be within or out of the range of the maximum and minimum threshold values.

In some implementations, the mask apparatus 1 can determine the kind of breathing state by comparing the time difference Tavg between a time Tmax at which the maximum pressure value Pmax is sensed and a time Tmin at which the minimum pressure value Pmin is sensed with the reference time.

For example, when the time difference Tavg is greater than a first reference time and less than a second reference time that is greater than the first reference time, it can be determined that the breathing is in the stable state.

Here, the first reference time can be defined as a minimum threshold time for determining whether the breathing is in the stable state, and the second reference time can be defined as a maximum threshold time for determining whether the breathing is in the stable state. That is, in general, in the stable breathing state, the time difference Tavg can be a time greater than the first reference time and less than the second reference time.

As a result of the determination, when it is determined that the breathing is not in the stable state, i.e., when it is determined that the breathing is in an unstable state, the controller of the mask apparatus 1 can perform the operation after the operation S11 again.

In detail, before returning to the operation S11, a fan module control algorithm applied when the breathing is in the unstable state can be performed, and then the operation S11 in which the pressure inside the mask is sensed again can be performed. The fan module control algorithm applied when the breathing is in the unstable state will be described in detail in FIG. 15.

Alternatively, if it is determined that the breathing is not in the stable state, the fan module can be controlled to rotate at a default speed (e.g., the low speed) unconditionally.

On the other hand, when it is determined that the breathing is in the stable state, an inhalation time Ti is calculated using the time difference Tavg between a time corresponding to the maximum pressure value Pmax and a time corresponding to the minimum pressure value Pmin (S14).

Here, since the inhalation time Ti means a time while the user's inhalation is continuous actually, it can be a time corresponding to the time difference Tavg. In general, when the exhalation is finished, the inhalation does not start immediately, an apnea time is maintained for a short time. Thus, the inhalation time Ti can be understood as a time that is shorter than the time difference Tavg, but In some examples, the inhalation time Ti is defined as the same time as the time difference Tavg.

In some implementations, the controller of the mask apparatus 1 calculates a tidal volume once by using the calculated difference value Pavg and the inhalation time Ti (S15).

In some implementations, the tidal volume can be defined by Equation 1 below.

$$\text{TidalVolume} = \alpha \times \text{Tavg} \times (\text{Pmax} - \text{Pmin}) \qquad \text{<Equation 1>}$$

Here, is "α" constant, "Tavg" is an average time difference between the time Tmax corresponding to the maximum pressure value and the time Tmin corresponding to the minimum pressure value, and "Pmax" is the maximum pressure value or an average value of the maximum pressure values, and "Pmin" is the minimum pressure value or an average value of the minimum pressure values.

A unit of the tidal volume can be "ml," a unit of "Tavg" can be seconds (sec), and a unit of each of "Pmax" and "Pmin" can be Pascal (Pa). The constant "α" is a constant used to determine whether the user breathes in the stable state and also is a preset value.

That is, when it is determined that the breathing is stable, the mask apparatus 1 can calculate the tidal volume by substituting information detected by the pressure sensor 14 and the processed information into Equation 1.

The mask apparatus 1 controls the rotation speed of the fan module based on the calculated tidal volume Vt and inhalation time Ti (S16).

Particularly, the mask apparatus 1 can control the rotation speed of the fan motor 180 by using a correction value (or compensation value) Vt/Ti obtained by dividing the calculated tidal volume Vt by the inhalation time Ti, i.e., ventilation per unit time (ml/s).

The reason for controlling the rotation speed of the fan motor 180 using the ventilation per unit time is that the correction value Vt/Ti, i.e., the ventilation per unit time has little variation among individuals and thus has tendency to converge to a specific value. This is to easily control the fan motor 180 through the rotation speed. The tendency of most convergence to the specific value can be defined as high convergence (or high convergence degree).

That is, when the fan motor 180 is controlled according to the correction value Vt/Ti, even if the user performs the heavy exercise, an appropriate ventilation can be provided accordingly. For example, the mask apparatus 1 can control the rotation speed of the fan motor 180 in proportion to the correction value Vt/Ti.

Here, when the correction value Vt/Ti is large, it can mean that the exercise intensity is relatively large. That is, the higher the exercise intensity, the greater the required ventilation. In this case, the rotation speed of the fan motor 180 can be quickly controlled.

FIG. 15 is a detailed flowchart illustrating an example of a method for controlling a mask apparatus.

Referring to FIG. 15, the controller of the mask apparatus 1 detects the internal pressure of the mask using the pressure sensor 14 (S21) and extracts and store the maximum pressure value Pmax and the minimum pressure value Pmin among the sensed pressure values (S22).

In some implementations, the controller of the mask apparatus 1 extracts and stores a first time Tmax corresponding to the maximum pressure value Pmax and a second time Tmin corresponding to the minimum pressure value Pmin (S23).

In some implementations, the controller of the mask apparatus 1 determines whether the difference value Pavg between the maximum pressure value Pmax and the minimum pressure value Pmin is greater than the first reference value P1 and less than the second reference value P2 (S24).

Here, the reason for determining whether the difference value Pavg between the maximum pressure value Pmax and the minimum pressure value Pmin is greater than the first reference value P1 and less than the second reference value P2 is for determining whether the user's breathing pressure has an amplitude in the stable breathing state.

When the difference value Pavg is greater than the first reference value P1 and less than the second reference value P2 that is greater than the first reference value P1, the controller of the mask apparatus 1 determines whether the time difference Tavg between the time Tmax corresponding to the maximum pressure value and the time Tmin corresponding to the minimum pressure value is greater than the first reference time and less than the second reference time (S25).

Here, the reason for determining whether the time difference Tavg between the time Tmax corresponding to the maximum pressure value and the time Tmin corresponding to the minimum pressure value is greater than the first reference time and less than the second reference time is for determining whether the user's breathing cycle has a stable breathing cycle.

That is, the operations S24 and S25 can be understood as determining whether the user's breathing is in the stable state.

In detail, to determine whether the user's breathing is in the stable state, it can be determined by considering only the difference between the maximum pressure value and the minimum pressure value, and in addition, determined by considering the time difference between time points at which the maximum pressure value and the minimum pressure value are sensed. When the time difference Tavg between the time Tmax corresponding to the maximum pressure value and the time Tmin corresponding to the minimum pressure value is greater than the first reference time and less than the second reference time, the controller of the mask apparatus 1 determines whether the number of times of attempts (n) to determine the stable breathing reaches the number of times of reference (N) or the number of times of setting (S27) after increasing in number of times of attempts (n) to extract and store the maximum and minimum pressure values once.

Here, the reason for determining whether the number of times of attempts (n) for determining the stable breathing reaches the number of times of reference (N) is for securing a certain amount of breathing cycle data for determining the stable breathing. That is, as more breathing cycle data is accumulated, accuracy can increase.

The number of times of reference (N) can be, for example, about 10 times. In some examples, the number of times of reference can be set at various times by the user or a designer.

If the number of times of attempts (n) to determine the stable breathing reaches the number of times of reference (N), the controller of the mask apparatus 1 calculate an average value for each maximum pressure value Pmax, and each minimum pressure value Pmin (S28).

In some implementations, the controller of the mask apparatus 1 calculates the average time Tavg of the differences between the first time Tmax corresponding to each maximum pressure value and the second time Tmin corresponding to each minimum pressure value (S29).

Then, the controller of the mask apparatus 1 calculates the tidal volume Vt using the calculated information (S30).

As shown in Equation 1 described above, the mask apparatus 1 substitutes the average value Pmax for the maximum pressure value, the average value Pmin for the minimum pressure value, and the average time Tavg into Equation once to calculate the ventilation Vt.

In some implementations, the mask apparatus 1 stores and updates the calculated tidal volume information in the memory 190 (S31). In some implementations, the controller of the mask apparatus 1 can control the rotation speed of the fan motor 180 with reference to the updated memory 190 (S32).

Particularly, the mask apparatus 1 controls the rotation speed of the fan motor 180 using the correction value Vt/Ti obtained by dividing the calculated tidal volume Vt by the inhalation time Ti.

The reason for controlling the rotation speed of the fan motor 180 using the correction value Vt/Ti that is obtained by dividing the tidal volume Vt by the inhalation time (Ti) is for controlling the fan motor 180 through a very high convergence tendency because the correction value Vt/Ti has the very high convergence tendency.

That is, when the fan motor 180 is controlled according to the correction value Vt/Ti, even if the user performs the heavy exercise, an appropriate ventilation can be provided accordingly. For example, the mask apparatus 1 can control the rotation speed of the fan motor 180 in proportion to the correction value Vt/Ti.

Here, when the correction value Vt/Ti is large, it means that the exercise intensity is relatively large, and thus the rotation speed of the fan motor 180 can be controlled in proportion to the correction value Vt/Ti.

In operation S27, when the number of times attempts (n) to determine the stable breathing does not reach the number of times of reference (N), the mask apparatus 1 can control the rotation speed of the fan motor 180 based on the existing data stored in the memory 190, i.e., the tidal volume before the update and then proceed to the next operation (S33).

That is, if it is determined that the breathing data for determining whether the breathing is in the stable state is determined to be insufficient, the rotation speed of the fan motor 180 is controlled with reference to the tidal volume data before the update stored in the memory 190 without recalculating the tidal volume.

In some implementations, while the fan motor 180 is being controlled or when the control of the fan motor 180 is completed, the controller of the mask apparatus 1 determines whether a mask power-off command is input (S33). When the mask power-off command is input, the driving of the fan motor 180 can be stopped by turning off the power of the mask.

If the mask power-off command is not input in operation S33, the mask apparatus 1 can perform the operations described above in operation S21 again.

That is, unless the mask power-off command is input, the mask apparatus 1 can continuously senses the internal pressure of the mask using the pressure sensor 14 and periodically calculate and update the tidal volume Vt using the sensed information.

According to this configuration, since the rotation speed of the fan is appropriately adjusted according to the user's breathing pattern or exercise state, there is an advantage that the breathing is more comfortable.

In operation S24, when the difference value Pavg between the maximum pressure value and the minimum pressure value is not a value between the first reference value P1 and the second reference value P2, the controller of the mask apparatus 1 determines whether the difference value Pavg between the maximum pressure value and the minimum pressure value exceeds the second reference value P2 (S34).

Particularly, that the difference value Pavg is greater than the second reference value P2 can mean a state in which the user is in the exercise state or a state in which the external air pressure is rapidly changed.

That is, when the user exercises, since the breathing gasps, the difference value Pavg between the maximum pressure value Pmax and the minimum pressure value Pmin can increase significantly.

In some examples, when the user boards on an elevator to move up or down, the difference between the external air pressures can be changed rapidly, and thus the difference value Pavg between the maximum pressure value Pmax and the minimum pressure value Pmin can increase significantly.

As described above, the mask apparatus 1 determines that the breathing is not in the stable state when the difference value Pavg between the maximum pressure value Pmax and the minimum pressure value Pmin is changed significantly, initializes the number of times of extraction and storage of the maximum and minimum pressure values and, i.e., the number of times of attempts (n), and initialize the measured pressure values (S36). That is to say, in a situation in which the breathing is not in the stable state, the time difference may not be calculated, or the pressure data for the calculation of the tidal volume may not be accumulated.

In some implementations, the controller of the mask apparatus 1 can control the rotation speed of the motor with reference to the previously updated tidal volume data or the information stored in the memory 190 (S41) and then proceed to operation S33.

On the other hand, in operation S34, when the difference value Pavg between the maximum pressure value and the minimum pressure value is less than the first reference value P1, the controller of the mask apparatus 1 recognizes that the user does not wear the mask.

Particularly, that the difference value Pavg is less than the first reference value P1 can be understood as a state in which the user's breathing is not sensed, i.e., a state in which the user removes the mask.

That is, since the breathing is not sensed in the state in which the user removes the mask, the difference value Pavg between the maximum pressure value Pmax and the minimum pressure value Pmin can be insignificant.

As described above, when the difference value Pavg between the maximum pressure value Pmax and the minimum pressure value Pmin is very small, the controller of the mask apparatus 1 determines that the mask is not worn and then initializes the number of times of attempts (n) of the extraction and storage of the pressure values for determining the stable breathing and initializes the measured pressure values (S38).

In some implementations, after stopping the operation of the fan motor 180 (S39), the controller of the mask apparatus 1 can proceed to the next operation S33.

On the other hand, in operation S25, if the time difference Tavg between the time Tmax corresponding to the maximum pressure value and the time Tmin corresponding to the minimum pressure value is not a value between the first reference time and the second reference time, in operation S40, the mask apparatus 1 determines whether the time difference Tavg is greater than the second reference time.

Particularly, even though the pressure difference Pavg is within the stabilization range, the fact that the time difference Tavg is greater than the second reference time can mean that the user is in a state in which the user breathes deeply in the stable state.

That is, when the deep breathing while wearing the mask, the time difference Tavg, i.e., the inhalation time Ti can be lengthened.

As described above, the controller of the mask apparatus 1 determines the breathing is in the deep breathing state when the inhalation time Ti is greater than the inhalation time in the stabilization state and then initializes the number of times of attempts (n) of the extraction and storage of the maximum and minimum pressure values and initializes the measured pressure values (S36). In some implementations, the controller of the mask apparatus 1 can control the fan motor based on the ventilation data before the update (S41).

On the other hand, even though the pressure difference Pavg is within the stabilization range, when the time difference Tavg is less than the first reference time, the controller of the mask apparatus 1 recognizes this state as a state in which the user is breathing abnormally, or the mask apparatus 1 abnormally operates.

Particularly, that the time difference Tavg is less than the first reference time can be understood as abnormally rapid breathing or a malfunction in the mask or the sensor.

As described above, in operation S40, when the time difference Tavg between the first time Tmax and the second time Tmin is very small, the controller of the mask apparatus 1 determines that it is in an abnormal breathing state, and then, under the condition that the mask is not worn in the same manner as in the fan motor control process, the number of times of attempts (n) of the extraction and storage of the maximum and minimum pressure values is initialized (S37), and the measured pressure values are initialized (S38).

In some implementations, after stopping the operation of the fan motor 180 (S39), the controller of the mask apparatus 1 can proceed to the operation S33.

According to the configuration In some examples, the rotation speed of the fan can be appropriately driven according to the user's breathing pattern or the exercise state. In some implementations, the user's exercise intensity, the breathing state, the external environment change, or the malfunction of the machine can be determined using the pressure value according to the user's breathing, and thus, the appropriate driving can be performed.

What is claimed is:

1. A mask apparatus comprising:
a mask body configured to mount a fan module;
a seal coupled to a rear surface of the mask body, the seal being configured to define a breathing space therein;
a pressure sensor coupled to the mask body and configured to sense air pressure in the breathing space;
a mask body cover that is coupled to a front surface of the mask body and covers the fan module; and
a controller coupled to the mask body and configured to control a rotation speed of the fan module based on pressure values measured by the pressure sensor,
wherein the controller is configured to:
determine breathing information comprising a maximum pressure value and a minimum pressure value among the pressure values, a maximum time point corresponding to the maximum pressure value, and a minimum time point corresponding to the minimum pressure value,
determine a breathing state of a user based on the breathing information,
determine whether the breathing state is a steady state,
determine a tidal volume of the user based on the breathing information, wherein the tidal volume represents a volume of air that the user breathes in and out in the steady state,
control the rotation speed of the fan module based on the tidal volume,
determine a difference value between the maximum pressure value and the minimum pressure value,
compare the difference value to a reference value, and
determine the breathing state based on comparing the difference value to the reference value, wherein the reference value comprises:
a first reference value, and
a second reference value greater than the first reference value, and wherein the controller is configured to:
determine that the breathing state is the steady state based on the difference value being greater than the first reference value and less than the second reference value,
based on the difference value being greater than the second reference value, determine that the breathing state is an exercise state, and
based on determining that the breathing state is the exercise state, reset the measured pressure values and control the rotation speed of the fan module based on tidal volume data stored before the breathing state is the exercise state.

2. The mask apparatus according to claim 1, wherein the controller is configured to:
determine a time difference between the maximum time point and the minimum time point;
compare the time difference to a reference time; and
determine the breathing state based on comparing the time difference to the reference time.

3. The mask apparatus according to claim 2, wherein the reference time comprises:
a first reference duration; and
a second reference duration greater than the first reference duration, and
wherein the controller is configured to determine that the breathing state is the steady state based on the time difference being greater than the first reference duration and less than the second reference duration.

4. The mask apparatus according to claim 3, wherein the controller is configured to, based on determining that the breathing state is the steady state, determine the tidal volume by using the difference value and the time difference.

5. The mask apparatus according to claim 4, wherein the controller is configured to:
determine a breathing volume per unit time that is defined by dividing the tidal volume by the time difference; and
control the rotation speed of the fan module based on the breathing volume per unit time.

6. The mask apparatus according to claim 4, wherein the controller is configured to:
determine (i) a mean maximum pressure value of a plurality of maximum pressure values sensed during the steady state, (ii) a mean minimum value of a plurality of minimum pressure values sensed during the steady state, and (iii) a mean time difference determined based on a plurality of time differences, wherein each time difference corresponds to a difference between time points corresponding to one of the plurality of maximum pressure values and one of the plurality of minimum pressure values; and
determine the tidal volume based on the mean maximum pressure value, the mean minimum value, and the mean time difference.

7. The mask apparatus according to claim 4, wherein the controller is configured to:
store information of the tidal volume in a non-transitory memory;
update the information of the tidal volume; and
control the rotation speed of the fan module based on the updated information of the tidal volume.

8. The mask apparatus according to claim 3, wherein the controller is configured to:

based on the time difference being greater than the second reference duration, determine that the user is in a deep breathing state; and
based on determining that the user is in the deep breathing state, reset the measured pressure values and control the rotation speed of the fan module based on tidal volume data stored before the user is in the deep breathing state.

9. The mask apparatus according to claim 3, wherein the controller is configured to:
based on the time difference being less than the first reference duration, determine that the user is in an abnormal breathing state or that the mask apparatus is in a malfunction state; and
based on determining that the user is in the abnormal breathing state or that the mask apparatus is in the malfunction state, reset the measured pressure values and stop operation of the fan module.

10. The mask apparatus according to claim 1, wherein the controller is configured to:
based on the difference value being less than the first reference value, determine that the mask apparatus is not worn by the user; and
based on determining that the mask apparatus is not worn by the user, reset the measured pressure values and stop operation of the fan module.

11. A method for controlling a mask apparatus, the method comprising:
sensing an internal pressure of the mask apparatus by a pressure sensor;
determining breathing information comprising a maximum pressure value and a minimum pressure value among pressure values measured by the pressure sensor, a maximum time point corresponding to the maximum pressure value, and a minimum time point corresponding to the minimum pressure value;
storing the breathing information;
determining a breathing state of a user based on the breathing information;
determining whether the breathing state is a steady state;
determining a tidal volume of the user based on the breathing information, wherein the tidal volume represents a volume of air that the user breathes in and out when the breathing state is the steady state; and
controlling a rotation speed of a fan module of the mask apparatus based on the tidal volume,
wherein determining the breathing state comprises:
determining a difference value between the maximum pressure value and the minimum pressure value,
comparing the difference value to a reference value,
determining the breathing state based on comparing the difference value to the reference value, wherein the reference value comprises a first reference value and a second reference value greater than the first reference value,
determining that the breathing state is the steady state based on the difference value being greater than the first reference value and less than the second reference value, and
determining that the breathing state is an exercise state based on the difference value being greater than the second reference value,
wherein the method further comprises resetting the measured pressure values based on determining that the breathing state is the exercise state, and
wherein controlling the rotation speed of the fan module comprises controlling the rotation speed of the fan module based on tidal volume data stored before the breathing state is the exercise state.

12. The method according to claim 11, wherein determining the breathing state comprises:
- determining a time difference between the maximum time point and the minimum time point;
- comparing the time difference to a reference time;
- determining the breathing state based on comparing the time difference to the reference time, wherein the reference time comprises a first reference duration and a second reference duration greater than the first reference duration; and
- determining that the breathing state is the steady state based on the time difference being greater than the first reference duration and less than the second reference duration.

13. The method according to claim 12, wherein determining the tidal volume comprises calculating an equation that has the difference value and the time difference as variables, and
- wherein controlling the rotation speed of the fan module comprises:
- determining a breathing volume per unit time that is defined by dividing the tidal volume by the time difference, and
- controlling the rotation speed of the fan module based on the breathing volume per unit time.

14. The method according to claim 13, wherein determining the breathing information compresses:
- determining (i) a mean maximum pressure value of a plurality of maximum pressure values sensed during the steady state, (ii) a mean minimum value of a plurality of minimum pressure values sensed during the steady state, and (iii) a mean time difference determined based on a plurality of time differences, wherein each time difference corresponds to a difference between time points corresponding to one of the plurality of maximum pressure values and one of the plurality of minimum pressure values.

15. The method according to claim 13, further comprising:
- storing information of the tidal volume in a non-transitory memory; and
- updating the information of the tidal volume,
- wherein controlling the rotation speed of the fan module comprises controlling the rotation speed of the fan module based on the updated information of the tidal volume.

16. The method according to claim 12, further comprising:
- based on the time difference being greater than the second reference duration, determining that the user is in a deep breathing state; and
- based on determining that the user is in the deep breathing state, resetting the measured pressure values and controlling the rotation speed of the fan module based on tidal volume data stored before the user is in the deep breathing state.

17. The method according to claim 12, further comprising:
- based on the time difference being less than the first reference duration, determining that the user is in an abnormal breathing state or that the mask apparatus is in a malfunction state; and
- based on determining that the user is in the abnormal breathing state or that the mask apparatus is in the malfunction state, resetting the measured pressure values and stopping operation of the fan module.

18. The method according to claim 11, further comprising:
- based on the difference value being less than the first reference value, determining that the mask apparatus is not worn by the user; and
- based on determining that the mask apparatus is not worn by the user, resetting the measured pressure values and stopping operation of the fan module.

\* \* \* \* \*